(12) United States Patent
Lee et al.

(10) Patent No.: US 7,691,865 B2
(45) Date of Patent: *Apr. 6, 2010

(54) PYRAZOLOPYRIDINES AND METHODS OF MAKING AND USING THE SAME

(75) Inventors: Wen-Cherng Lee, Lexington, MA (US); Mary Beth Carter, Arlington, MA (US); Lihong Sun, Arlington, MA (US); Paul Lyne, Arlington, MA (US); Claudio Chuaqui, Somerville, MA (US); Zhongli Zheng, Lexington, MA (US); Juswinder Singh, Ashland, MA (US); Paula Boriack-Sjodin, Waltham, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 416 days.

This patent is subject to a terminal disclaimer.

(21) Appl. No.: 10/526,839

(22) PCT Filed: Sep. 5, 2003

(86) PCT No.: PCT/US03/27722

§ 371 (c)(1), (2), (4) Date: Nov. 1, 2005

(87) PCT Pub. No.: WO2004/022054

PCT Pub. Date: Mar. 18, 2004

(65) Prior Publication Data

US 2006/0106033 A1    May 18, 2006

Related U.S. Application Data

(60) Provisional application No. 60/408,811, filed on Sep. 6, 2002.

(51) Int. Cl.
*A61K 31/519* (2006.01)
*C07D 471/02* (2006.01)
*C07D 487/04* (2006.01)

(52) U.S. Cl. .................. 514/259.3; 514/303; 544/281; 546/117

(58) Field of Classification Search ............... None
See application file for complete search history.

(56) References Cited

U.S. PATENT DOCUMENTS

| | | |
|---|---|---|
| 3,940,486 A | 2/1976 | Fitzi |
| 4,302,464 A | 11/1981 | LaMattina et al. |
| 4,686,231 A | 8/1987 | Bender et al. |
| 5,514,505 A | 5/1996 | Limburg et al. |
| 5,593,991 A | 1/1997 | Adams et al. |
| 5,593,992 A | 1/1997 | Adams et al. |
| 5,604,240 A | 2/1997 | Chambers et al. |
| 5,656,644 A | 8/1997 | Adams et al. |
| 5,658,903 A | 8/1997 | Adams et al. |
| 5,663,334 A | 9/1997 | Sheldrake et al. |
| 5,670,527 A | 9/1997 | Adams et al. |
| 5,686,455 A | 11/1997 | Adams et al. |
| 5,716,955 A | 2/1998 | Adams et al. |
| 5,717,100 A | 2/1998 | Selnick et al. |
| 5,739,143 A | 4/1998 | Adams et al. |
| 5,756,499 A | 5/1998 | Adams et al. |
| 5,792,778 A | 8/1998 | De Laszlo et al. |
| 5,811,549 A | 9/1998 | Adams et al. |
| 5,837,719 A | 11/1998 | De Laszlo et al. |
| 5,854,264 A | 12/1998 | Anthony et al. |
| 5,854,265 A | 12/1998 | Anthony et al. |
| 5,854,276 A | 12/1998 | Okudaira et al. |
| 5,859,041 A | 1/1999 | Liverton et al. |
| 5,864,036 A | 1/1999 | Adams et al. |
| 5,869,660 A | 2/1999 | Adams et al. |
| 5,872,136 A | 2/1999 | Anthony et al. |
| 5,880,140 A | 3/1999 | Anthony et al. |
| 5,883,105 A | 3/1999 | Anthony et al. |
| 5,916,891 A | 6/1999 | Adams et al. |
| 5,917,043 A | 6/1999 | Sisco et al. |
| 5,932,576 A | 8/1999 | Anantanarayan et al. |
| 5,939,439 A | 8/1999 | Anthony et al. |
| 5,939,557 A | 8/1999 | Anthony et al. |
| 5,965,583 A | 10/1999 | Beers et al. |
| 5,969,184 A | 10/1999 | Adams et al. |

(Continued)

FOREIGN PATENT DOCUMENTS

EP        1317448        5/2005

(Continued)

OTHER PUBLICATIONS

STN abstract of JP 05-017470 in English with structures; CAPLUS Accession # 1993:472619; Accessed Jul. 9, 2007.*

(Continued)

*Primary Examiner*—Brian-Yong S Kwon
(74) *Attorney, Agent, or Firm*—Honigman, Miller, Schwartz & Cohn LLP; Thomas A. Wootton; Jonathan P. O'Brien

(57) ABSTRACT

Compounds of formula I possess unexpectedly high affinity for Alk 5 and/or Alk 4, and can be useful as antagonists thereof for preventing and/or treating numerous diseases, including fibrotic disorders. In one embodiment, the invention features a compound of formula I:

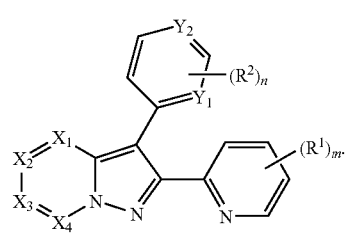

(I)

11 Claims, No Drawings

U.S. PATENT DOCUMENTS

| | | | |
|---|---|---|---|
| 5,977,103 | A | 11/1999 | Adams et al. |
| 5,998,425 | A | 12/1999 | Adams et al. |
| 6,040,320 | A | 3/2000 | Beers et al. |
| 6,046,208 | A | 4/2000 | Adams et al. |
| 6,051,574 | A | 4/2000 | Anthony et al. |
| 6,077,853 | A | 6/2000 | Graham et al. |
| 6,080,870 | A | 6/2000 | Anthony et al. |
| 6,083,949 | A | 7/2000 | Liverton et al. |
| 6,087,381 | A | 7/2000 | Hanson et al. |
| 6,096,739 | A | 8/2000 | Feuerstein et al. |
| 6,096,748 | A | 8/2000 | Gallagher et al. |
| 6,100,399 | A | 8/2000 | Sisco et al. |
| 6,103,936 | A | 8/2000 | Adams et al. |
| 6,136,828 | A | 10/2000 | Elliott et al. |
| 6,150,557 | A | 11/2000 | Adams et al. |
| 6,180,643 | B1 | 1/2001 | Zablocki et al. |
| 6,214,844 | B1 | 4/2001 | Adams et al. |
| 6,218,537 | B1 | 4/2001 | Adams et al. |
| 6,222,036 | B1 | 4/2001 | Peng et al. |
| 6,235,760 | B1 | 5/2001 | Feuerstein et al. |
| 6,239,279 | B1 | 5/2001 | Sisko et al. |
| 6,255,491 | B1 | 7/2001 | Sisko et al. |
| 6,268,370 | B1 | 7/2001 | Adams et al. |
| 6,288,089 | B1 | 9/2001 | Zawada et al. |
| 6,300,347 | B1 | 10/2001 | Revesz et al. |
| 6,335,336 | B1 | 1/2002 | Anantanarayan et al. |
| 6,335,340 | B1 | 1/2002 | Gallagher |
| 6,369,068 | B1 | 4/2002 | Adams et al. |
| 6,372,741 | B1 | 4/2002 | Jackson et al. |
| 6,387,898 | B1 | 5/2002 | Feuerstein et al. |
| 6,399,644 | B1 | 6/2002 | Wexler et al. |
| 6,410,729 | B1 | 6/2002 | Spohr et al. |
| 6,420,385 | B1 | 7/2002 | Spohr et al. |
| 6,423,713 | B1 | 7/2002 | Anantanarayan et al. |
| 6,440,973 | B1 | 8/2002 | Zablocki et al. |
| 6,465,493 | B1 | 10/2002 | Burgess et al. |
| 6,503,930 | B1 | 1/2003 | Hanson et al. |
| 6,511,997 | B1 | 1/2003 | Minami et al. |
| 6,514,977 | B1 | 2/2003 | Anantanarayan et al. |
| 6,525,059 | B1 | 2/2003 | Anantanarayan et al. |
| 6,528,512 | B1 | 3/2003 | Gallagher et al. |
| 6,548,503 | B1 | 4/2003 | Adams et al. |
| 6,562,832 | B1 | 5/2003 | Adams et al. |
| 6,579,873 | B2 | 6/2003 | Anantanarayan et al. |
| 6,579,874 | B2 | 6/2003 | Revesz et al. |
| 6,599,910 | B1 | 7/2003 | Adams et al. |
| 6,602,877 | B1 | 8/2003 | Bamborough et al. |
| 6,603,005 | B2 | 8/2003 | Baque et al. |
| 6,605,634 | B2 | 8/2003 | Zablocki et al. |
| 6,610,688 | B2 | 8/2003 | Liang et al. |
| 6,610,698 | B2 | 8/2003 | Spohr et al. |
| 6,617,324 | B1 | 9/2003 | Naraian et al. |
| 6,630,325 | B1 | 10/2003 | Lindner et al. |
| 6,645,989 | B2 | 11/2003 | Adams et al. |
| 6,649,604 | B2 | 11/2003 | Spohr et al. |
| 6,667,325 | B1 | 12/2003 | Minami et al. |
| 6,689,770 | B2 | 2/2004 | Wexler et al. |
| 6,727,364 | B2 | 4/2004 | Tullis et al. |
| 6,730,683 | B2 | 5/2004 | Gallagher |
| 6,774,127 | B2 | 8/2004 | Adams et al. |
| 6,787,555 | B2 | 9/2004 | Tullis et al. |
| 6,852,740 | B2 | 2/2005 | Hanson et al. |
| 6,855,719 | B1 | 2/2005 | Thomas et al. |
| 6,861,417 | B2 | 3/2005 | Adams et al. |
| 6,903,217 | B2 | 6/2005 | Bacqué et al. |
| 7,199,120 | B2 * | 4/2007 | Gudmundsson et al. .. 514/235.8 |
| 2002/0032183 | A1 | 3/2002 | LoGrasso et al. |
| 2002/0049220 | A1 | 4/2002 | Revesz et al. |
| 2002/0086869 | A1 | 7/2002 | Anantanarayan et al. |
| 2002/0103202 | A1 | 8/2002 | Pinto et al. |
| 2002/0111492 | A1 | 8/2002 | Baque et al. |
| 2002/0123500 | A1 | 9/2002 | Jackson et al. |
| 2002/0156104 | A1 | 10/2002 | Adams et al. |
| 2002/0161211 | A1 | 10/2002 | Lindner et al. |
| 2002/0183319 | A1 | 12/2002 | Liang et al. |
| 2002/0198206 | A1 | 12/2002 | Gallagher |
| 2003/0013712 | A1 | 1/2003 | Tullis et al. |
| 2003/0050315 | A1 | 3/2003 | Wexler et al. |
| 2003/0069243 | A1 | 4/2003 | Adams et al. |
| 2003/0069425 | A1 | 4/2003 | Spohr et al. |
| 2003/0073704 | A1 | 4/2003 | Spohr et al. |
| 2003/0078274 | A1 | 4/2003 | Lipton et al. |
| 2003/0096819 | A1 | 5/2003 | Zablocki et al. |
| 2003/0100558 | A1 | 5/2003 | Tullis et al. |
| 2003/0113787 | A1 | 6/2003 | Bertin |
| 2003/0114452 | A1 | 6/2003 | Adams et al. |
| 2003/0144529 | A1 | 7/2003 | Hanson et al. |
| 2003/0149277 | A1 | 8/2003 | Gaster et al. |
| 2003/0153569 | A1 | 8/2003 | Adams et al. |
| 2003/0153588 | A1 | 8/2003 | Steadman et al. |
| 2003/0158238 | A1 | 8/2003 | Hale et al. |
| 2003/0166633 | A1 | 9/2003 | Gaster et al. |
| 2003/0191116 | A1 | 10/2003 | Kalindjian et al. |
| 2003/0207885 | A1 | 11/2003 | Hutchison et al. |
| 2003/0229110 | A1 | 12/2003 | Adams et al. |
| 2004/0014776 | A1 | 1/2004 | Breault et al. |
| 2004/0014973 | A1 | 1/2004 | Adams et al. |
| 2004/0038856 | A1 | 2/2004 | Chakravarty et al. |
| 2004/0038964 | A1 | 2/2004 | Dean et al. |
| 2004/0038991 | A1 | 2/2004 | Bamborough et al. |
| 2004/0039198 | A1 | 2/2004 | Bender et al. |
| 2004/0053924 | A1 | 3/2004 | Liang et al. |
| 2004/0053942 | A1 | 3/2004 | Alberti et al. |
| 2004/0053943 | A1 | 3/2004 | Adams et al. |
| 2004/0063176 | A1 | 4/2004 | Lindner et al. |
| 2004/0063745 | A1 | 4/2004 | Gellibert |
| 2004/0063949 | A1 | 4/2004 | Gellibert |
| 2004/0077687 | A1 | 4/2004 | Gellibert |
| 2004/0087623 | A1 | 5/2004 | Gellibert |
| 2004/0087628 | A1 | 5/2004 | Minami et al. |
| 2004/0097502 | A1 | 5/2004 | Gellibert |
| 2004/0106608 | A1 | 6/2004 | Munchhof et al. |
| 2004/0110797 | A1 | 6/2004 | Munchhof et al. |
| 2004/0147518 | A1 | 7/2004 | Bacque et al. |
| 2004/0147579 | A1 | 7/2004 | Naraian et al. |
| 2004/0152738 | A1 | 8/2004 | Gaster et al. |
| 2004/0157861 | A1 | 8/2004 | Scarborough et al. |
| 2004/0176390 | A1 | 9/2004 | Blumberg et al. |
| 2004/0176433 | A1 | 9/2004 | Naraian et al. |
| 2004/0214816 | A1 | 10/2004 | Beers et al. |
| 2004/0220230 | A1 | 11/2004 | Gaster et al. |
| 2004/0248903 | A1 | 12/2004 | Gudmundsson et al. |
| 2004/0266842 | A1 | 12/2004 | Gaster et al. |
| 2005/0176789 | A1 | 8/2005 | Hadida Ruah et al. |

FOREIGN PATENT DOCUMENTS

| | | | |
|---|---|---|---|
| GB | 2306108 | | 4/1997 |
| JP | 05-017470 | * | 1/1993 |
| WO | WO 9716426 | | 5/1977 |
| WO | WO 9216527 | | 10/1992 |
| WO | WO 9502591 | | 1/1995 |
| WO | WO 9503297 | | 2/1995 |
| WO | WO 9618626 | | 6/1996 |
| WO | WO 9621452 | | 7/1996 |
| WO | WO 9640143 | | 12/1996 |
| WO | WO 9716441 | | 5/1997 |
| WO | WO 9723479 | | 7/1997 |
| WO | WO 9725046 | | 7/1997 |
| WO | WO 9736582 | | 10/1997 |
| WO | WO 9825619 | | 6/1998 |
| WO | WO 9857966 | | 12/1998 |
| WO | WO 9903480 | | 1/1999 |
| WO | WO 9918942 | | 4/1999 |

| | | |
|---|---|---|
| WO | WO 9958128 | 11/1999 |
| WO | WO 9961437 | 12/1999 |
| WO | WO 0001688 | 1/2000 |
| WO | WO 0023444 | 4/2000 |
| WO | WO 00/26216 | 5/2000 |
| WO | WO 0026209 | 5/2000 |
| WO | WO 0033836 | 6/2000 |
| WO | WO 0122965 | 4/2001 |
| WO | WO 0137835 | 5/2001 |
| WO | WO 0138324 | 5/2001 |
| WO | WO 0200651 | 1/2002 |
| WO | WO 02055077 | 7/2002 |
| WO | WO 02062793 | 8/2002 |
| WO | WO 02087591 | 11/2002 |
| WO | WO 02088107 | 11/2002 |
| WO | WO 02092593 | 11/2002 |
| WO | WO 03015781 | 2/2003 |
| WO | WO 03062215 | 7/2003 |
| WO | WO 03087304 | 10/2003 |
| WO | WO 03091226 | 11/2003 |
| WO | WO 2004005264 | 1/2004 |
| WO | WO 2004005282 | 1/2004 |
| WO | WO 2004011642 | 2/2004 |
| WO | WO 2004013125 | 2/2004 |
| WO | WO 2004013135 | 2/2004 |
| WO | WO 2004013138 | 2/2004 |
| WO | WO 2004016606 | 2/2004 |
| WO | WO 2004021989 | 3/2004 |
| WO | WO 2004026307 | 4/2004 |
| WO | WO 2004029043 | 4/2004 |
| WO | WO 2004048382 | 6/2004 |
| WO | WO 2004065392 | 8/2004 |
| WO | WO 2004111036 | 12/2004 |
| WO | WO 2004111046 | 12/2004 |

OTHER PUBLICATIONS

Redondo, et al.; "TGF-beta1: a novel target for cardiovascular pharmacology"; 2007; Cytokine & Growth Factor Reviews; 18:279-286.*

Alexandrow, Mark G., and Moses, Harold L., "Transforming Growth Factor β and Cell Cycle Regulation," *Cancer Research*, 55: 1452-1457 (1995).

Blobe, Gerard C., et al., "Role of Transforming Growth Factor β in Human Disease," *The New England Journal of Medicine*, 342 (18): 1350-1358 (2000).

Border, Wayne A. and Noble, Nancy A., "Transforming Growth Factor β in Tissue Fibrosis," *The New England Journal of Medicine*, 331 (19): 1286-1292 (1994).

Border, Wayne A. and Ruoslahti Erkki, "Transforming Growth Factor β in Disease: The Dark Side of Tissue Repair," *J. Clin. Invest*, 90: 1-7 (1992).

Byfield, Stacey DaCosta, et al., "SB-505124 Is a Selective Inhibitor of Transforming Growth Factor-β Type I Receptors ALK4, ALK5, and ALK7," *Molecular Pharmacology*, 65 (3): 744-752 (2003).

Cipriano, Sherry C., et al., "Follistatin Is a Modulator of Gonadal Tumor Progression and the Activin-Induced Wasting Syndrome in Inhibin-Deficient Mice," *Endocrinology*, 141 (7): 2319-2327 (2000).

Coerver, Katherine A., et al., "Activin Signaling Through Activin Receptor Type II Causes the Cachexia-Like Symptoms in Inhibin-Deficient Mice," *Molecular Endocrinology*, 10: 534-543 (1996).

Dahly, Annette J., et al., "Antihypertensive Effects of Chronic Anti-TGF-β Antibody Therapy in Dahl S Rats," *American Journal. Physiological Regul. Integr. Comp. Physiol.*, 283: R757-767 (2002).

De Bleser, Pieter J., et al., "Localization and Cellular Sources of Activins in Normal and Fibrotic Rat Liver," *Hepatology*, 26: 905-912 (1997).

De Groot, Corline J. A., et al., "Expression of Transforming Growth Factor (TGF)-β1, -β2, and β3 Isoforms and TGF-β Type I and Type II Receptors in Multiple Sclerosis Lesions and Human Adult Astrocyte Cultures," *Journal of Neuropathology and Experimental Neurology*, 58 (2): 174-187 (1999).

Freireich, Emil J., et al., "Quantitative Comparison of Toxicity of Anticancer Agents in Mouse, Rat, Hamster, Dog, Monkey, and Man," *Cancer Chemotherapy Reports*, 50 (4): 219-244 (1996).

Hojo, Minoru, et al., "Cyclosporine Induces Cancer Progression by a Cell-Autonomous Mechanism," *Nature*, 397: 530-534 (1999).

Huang, Sheng-Tung and Gordon, Dana M., "Total synthesis of endothelin-converting enzyme antagonist WS75624 B," *Tetrahedron Letters*, 39 (51): 9335-9338 (1998).

Huse, Morgan, et al., "The TGFβ Receptor Activation Process: An Inhibitor- to Substrate-Binding Switch," *Molecular Cell*, 8: 671-682 (2001).

Inoue, Satoshi, et al., "Demonstration of Activin-A in Arteriosclerotic Lesions," *Biochemical and Biophysical Research Communications*, 205 (1): 441-448 (1994).

John, Gareth R., et al., "Multiple Sclerosis: Re-expression of a Developmental Pathway that Restricts Oligodendrocyte Maturation," *Nature. Medicine*, 8 (10): 1115-1121 (2002).

Journet, Michel, et al., "An Improved and Practical Procedure for the Synthesis of Substituted Phenylacetylpyridines," *Tetrahedron Letters*, 39: 1717-1720 (1998).

Krempen, Kimberly, et al., "Far Upstream Regulatory Elements Enhance Position-Independent and Uterus-Specific Expression of the Murine α1 (O). Collagen Promoter in Transgenic Mice," *Gene Expression*, 8: 151-163 (1999).

Laping, Nicholas J., "ALK5 Inhibition in Renal Disease," *Current Opinion in Pharmacology*, 3: 204-208 (2003).

Lecount, David J. and Jarvis, John A. J., "Reaction of 5-Chloropyridin-2-yl-thioureas with Phenacyl Bromides: A New Thiazole Synthesis. X-ray Crystal Structure of 5-(5-Chloropyridin-2-yl)-2-diethylamino-4-phenylthiazole," *Journal of the Chemical Society*, 1977, 8: 282-283 (1977).

Liverton, Nigel J., et al., "Design and Synthesis of Potent, Selective, and Orally Bioavailable Tetrasubstituted Imidazole Inhibitors of p38 Mitogen Activated Protein Kinase," *Journal of Medicinal Chemistry*, 42: 2180-2190 (1999).

Logan, Ann, et al., "Inhibition of Glial Scarring in the Injured Rat Brain by a Recombinant Human Monoclonal Antibody to Transforming Growth Factor-β2," *European Journal of Neuroscience*, 11: 2367-2374 (1999).

Logan, Ann et al., "Decorin Attenuates Gliotic Scar Formation in the Rat Cerebral Hemisphere," *Experimental Neurology*, 159: 504-510 (1999).

Maehara, Yoshihiko, et al., "Role of Transforming Growth Factor-β1 in Invasion and Metastasis in Gastric Carcinoma," *Journal of Clinical Oncology*, 17 (2): 607-614 (1999).

Masliah, Eliezer, et al., "Functional Role of TGFβ in Alzheimer's Disease Microvascular Injury: Lessons from Transgenic Mice," *Neurochemistry International*, 39: 393-400 (2001).

Massagué, Joan, "TGF-β Signal Transduction," *Annual Review Biochem. Med.* 67: 773-791 (1998).

Massagué, Joan, "The Transforming Growth Factor-β Family," *Annual Review Cell. Biol.*, 6: 594-641 (1990).

Matsuse, Takeshi, et al., "Expression of Immunoreactive Activin A Protein in Remodeling Lesions Associated with Interstitial Pulmonary Fibrosis," *American Journal of Pathology*, 148 (3): 707-713 (1996).

Matsuse, Takeshi, et al., "Expression of Immunoreactive and Bioactive Activin A Protein in Adult Murine Lung After Bleomycin Treatment," *American Journal of Respiratory Cell and Molecular Biology*, 13: 17-24 (1995).

Matzuk, M. M., et al., "Development of Cancer Cachexia-Like Syndrome and Adrenal Tumors in Inhibin-Deficient Mice," *Proc. Natl. Acad. Sci. USA* 91: 8817-8821 (1994).

Munz, Barbara, et al., "Overexpression of Activin A in the Skin of Transgenic Mice Reveals New Activities of Activin in Epidermal Morphogenesis, Dermal Fibrosis and Wound Repair," *The EMBO Journal*, 18 (19): 5205-5215 (1999).

Pawlowski, John E., et al., "Stimulation of Activin A Expression in Rat Aortic Smooth Muscle Cells by Thrombin and Angiotensin II Correlates with Neointimal Formation in Vivo," *J. Clin. Invest*. 100 (3): 639-648 (1997).

Picon, Antonio, et al., "A Subset of Metastatic Human Colon Cancers Expresses Elevated Levels of Transforming Growth Factor β1," *Cancer Epidemiology Biomarkers & Prevention*, 7: 497-504 (1998).

Revesz, Laszlo, et al., "SAR of 4-Hydroxypiperidine and Hydroxyalkyl Substituted Heterocycles as Novel p38 Map Kinase Inhibitors," *Bioorganic & Medicinal Chemistry Letters*, 10: 1261-1264 (2000).

Roberts, A. B. and Sporn M. B., "The Transforming Growth Factor-βs," *Peptide Growth Factors and Their Receptors* 95: 419-472 Berlin: Springer-Verlag (1990).

Roberts, Anita B. and Sporn Michael B., "Physiological Actions and Clinical Applications of Transforming Growth Factor-β (TGF-β)," *Growth Factors* 8: 1-9 (1993).

Rosendahl, Alexander, et al., "Activation of the TGF-β/Activin-Smad2 Pathway During Allergic Airway Inflammation," *American Journal of Respiratory Cell and Molecular Biology*, 25: 60-68 (2001).

Sugiyama, Motoya, et al., "Expression of Activin A is Increased in Cirrhotic and Fibrotic Rat Livers," *Gastroenterology*, 114: 550-558 (1998).

Xu, Shiwen, et al., "Scleroderma-Derived Human Fibroblasts Retain Abnormal Phenotypic and Functional Characteristics Following Retroviral Transduction with the SV40 tsT Antigen," *Experimental Cell Research*, 220: 407-414 (1995).

* cited by examiner

PYRAZOLOPYRIDINES AND METHODS OF MAKING AND USING THE SAME

This non-provisional application is a continuation application of PCT/US2003/027722, filed on Sep. 5, 2003, which is a continuation-in-part and claims benefit of priority of U.S. Provisional application 60/408,811, filed Sep. 6, 2002. The entire disclosure of each of the aforementioned patent applications are incorporated herein by reference.

BACKGROUND OF THE INVENTION

TGFβ (Transforming Growth Factor β) is a member of a large family of dimeric polypeptide growth factors that includes activins, inhibins, bone morphogenetic proteins (BMPs), growth and differentiation factors (GDFs) and mullerian inhibiting substance (MIS). TGFβ exists in three isoforms (TGFβ1, TGFβ2, and TGFβ3) and is present in most cells, along with its receptors. Each isoform is expressed in both a tissue-specific and developmentally regulated fashion. Each TGFβ isoform is synthesized as a precursor protein that is cleaved intracellularly into a C-terminal region (latency associated peptide (LAP)) and an N-terminal region known as mature or active TGFβ. LAP is typically non-covalently associated with mature TGFβ prior to secretion from the cell. The LAP-TGFβ complex cannot bind to the TGFβ receptors and is not biologically active. TGFβ is generally released (and activated) from the complex by a variety of mechanisms including interaction with thrombospondin-1 or plasmin.

Following activation, TGFβ binds at high affinity to the type II receptor (TGFβRII), a constitutively active serine/threonine kinase. The ligand-bound type II receptor phosphorylates the TGFβ type I receptor (Alk 5) in a glycine/serine rich domain, which allows the type I receptor to recruit and phosphorylate downstream signaling molecules, Smad2 or Smad3. See, e.g., Huse, M. et al., *Mol. Cell.* 8: 671-682 (2001). Phosphorylated Smad2 or Smad3 can then complex with Smad4, and the entire hetero-Smad complex translocates to the nucleus and regulates transcription of various TGFβ-responsive genes. See, e.g., Massagué, J. *Ann. Rev. Biochem. Med.* 67: 773 (1998).

Activins are also members of the TGFβ superfamily which are distinct from TGFβ in that they are homo- or heterodimers of activin βa or βb. Activins signal in a similar manner to TGFβ, that is, by binding to a constitutive serine-threonine receptor kinase, activin type II receptor (ActRIIB), and activating a type I serine-threonine receptor, Alk 4, to phosphorylate Smad2 or Smad3. The consequent formation of a hetero-Smad complex with Smad4 also results in the activin-induced regulation of gene transcription.

Indeed, TGFβ and related factors such as activin regulate a large array of cellular processes, e.g., cell cycle arrest in epithelial and hematopoietic cells, control of mesenchymal cell proliferation and differentiation, inflammatory cell recruitment, immunosuppression, wound healing, and extracellular matrix production. See, e.g., Massagué, J. *Ann. Rev. Cell. Biol.* 6: 594-641 (1990); Roberts, A. B. and Sporn M. B. *Peptide Growth Factors and Their Receptors*, 95: 419-472 Berlin: Springer-Verlag (1990); Roberts, A. B. and Sporn M. B. *Growth Factors* 8:1-9 (1993); and Alexandrow, M. G., Moses, H. L. *Cancer Res.* 55: 1452-1457 (1995). Hyperactivity of TGFβ signaling pathway underlies many human disorders (e.g., excess deposition of extracellular matrix, an abnormally high level of inflammatory responses, fibrotic disorders, and progressive cancers). Similarly, activin signaling and overexpression of activin is linked to pathological disorders that involve extracellular matrix accumulation and fibrosis (see, e.g., Matsuse, T. et al., *Am. J. Respir. Cell Mol. Biol.* 13: 17-24 (1995); Inoue, S. et al., *Biochem. Biophys. Res. Comm.* 205: 441-448 (1994); Matsuse, T. et al, *Am. J. Pathol.* 148: 707-713 (1996); De Bleser et al., *Hepatology* 26: 905-912 (1997); Pawlowski, J. E., et al., *J. Clin. Invest.* 100: 639-648 (1997); Sugiyama, M. et al., *Gastroenterology* 114: 550-558 (1998); Munz, B. et al., *EMBO J.* 18: 5205-5215 (1999)) and inflammatory responses (see, e.g., Rosendahl, A et al., *Am. J. Repir. Cell Mol. Biol.* 25: 60-68 (2001)). Studies have shown that TGFβ and activin can act synergistically to induce extracellular matrix (see, e.g., Sugiyama, M. et al., *Gastroenterology* 114: 550-558, (1998)). It is therefore desirable to develop modulators (e.g., antagonists) to signaling pathway components of the TGFβ family to prevent/treat disorders related to the malfunctioning of this signaling pathway.

SUMMARY OF THE INVENTION

Compounds of formula (I) are unexpectedly potent antagonists of the TGFβ family type I receptors, Alk5 and/or Alk 4. Thus, compounds of formula (I) can be employed in the prevention and/or treatment of diseases such as fibrosis (e.g., renal fibrosis, pulmonary fibrosis, and hepatic fibrosis), progressive cancers, or other diseases for which reduction of TGFβ family signaling activity is desirable.

In one aspect, the invention features a compound of formula I:

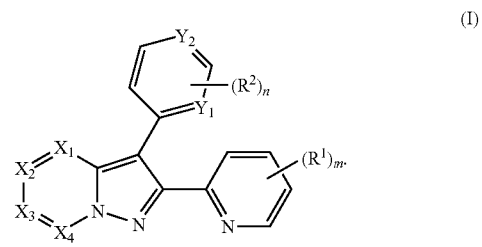

Each of $X_1$, $X_2$, $X_3$, and $X_4$ is independently $CR^x$ or N, provided that only two of $X_1$, $X_2$, $X_3$, and $X_4$ can be N simultaneously. Each of $Y_1$ and $Y_2$ is independently $CR^y$ or N, provided that at least one of $Y_1$ and $Y_2$ must be N. In other words, the ring having $Y_1$ and $Y_2$ ring atoms can be a pyrimidinyl or pyridyl. Each $R^1$ is independently alkyl alkenyl, alkynyl, alkoxy, acyl, halo, hydroxy, amino, nitro, cyano, guanadino, amidino, carboxy, sulfo, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaroyl. Each $R^2$ is independently alkyl, alkenyl, alkynyl, acyl, halo, hydroxy, —$NH_2$, —NH (alkyl), —N(alkyl)$_2$, —NH(cycloalkyl), —N(alkyl)(cycloalkyl), —NH(heterocycloalkyl), —NH(heteroaryl), —NH-alkyl-heterocycloalkyl, —NH-alkyl-heteroaryl, —NH(aralkyl), cycloalkyl, (cycloalkyl)alkyl, aryl, aralkyl, aroyl, heterocycloalkyl, (heterocycloalkyl)alkyl, heteroaryl, heteroaralkyl, heteroaroyl, nitro, cyano, guanadino, amidino, carboxy, sulfo, mercapto, alkoxy, cycloalkyloxy, cycloalkylalkoxy, aryloxy, arylalkoxy, heterocycloalkyloxy, (heterocycloalkyl)alkoxy, heteroaryloxy, heteroarylalkoxy, alkylsulfanyl, cycloalkylsulfanyl, (cycloalkyl)alkylsulfanyl, arylsulfanyl, aralkylsulfanyl, heterocycloalkylsulfanyl, (heterocycloalkyl)alkylsulfanyl, heteroarylsulfanyl, heteroaralkylsulfanyl, alkylsulfinyl, alkylsulfonyl, aminocarbonyl, aminosulfonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, alkoxycarbonylaminoalkylamino, (heteroaryl)arylcarbonylaminoalkylamino, heteroaralkylcarbonylaminoalkylamino, (heteroaryl)arylsulfonylaminoalkylcarbonylaminoalkylamino, arylsulfonylaminoalkylamino, alkoxycarbonyl, alkylcarbonyloxy, urea, thiourea, sulfamoyl, sulfamide, or carbamoyl. m is 0, 1, 2, 3, or 4; provided that when m≧2, two adjacent $R^1$ groups can join together to form a 4- to 8-membered optionally substituted cyclic moiety. n is 0, 1, 2, or 3, provided that when n≧2, two adjacent $R^2$ groups can join together to form a 4- to 8-membered optionally substituted cyclic moiety. See examples of the 4- to 8-membered optionally substituted cyclic moiety below. Each of $R^x$ and $R^y$ is independently hydrogen, alkyl, alkenyl, alkynyl, alkoxy, acyl, halo, hydroxy, amino, nitro, cyano, guanadino, amidino, carboxy, sulfo, mercapto, alkylsulfanyl, alkylsulfinyl, alkylsulfonyl, cycloalkylcarbonyl, (cycloalkyl)alkylcarbonyl, aroyl, aralkylcarbonyl, heterocycloalkylcarbonyl, (heterocycloalkyl)acyl, heteroaroyl, (heteroaryl)acyl, aminocarbonyl, alkylcarbonylamino, (amino)aminocarbonyl, alkylsulfonylaminocarbonyl, alkylsulfonylamino, cycloalkylcarbonylamino, cycloalkylsulfonylamino, (cycloalkyl)alkylcarbonylamino, (cycloalkyl)alkylsulfonylamino, arylcarbonylamino, arylsulfonylamino, aralkylcarbonylnamino, aralkylsulfonylamino, (heterocycloalkyl)carbonylamino, (heterocycloalkyl)sulfonylamino, (heterocycloalkyl)alkylcarbonylamino, (heterocycloalkyl)alkylsulfonylamino, heteroarylcarbonylamino, heteroarylsulfonylamino, heteroaralkylcarbonylamino, heteroaralkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, (cycloalkyl)alkyl, (cycloalkyl)alkoxy, (cycloalkyl)alkylsulfanyl, heterocycloalkyl, heterocycloalkyloxy, heterocycloalkylsulfanyl, (heterocycloalkyl)alkyl, (heterocycloalkyl)alkoxy, (heterocycloalkyl)alkylsulfanyl, aryl, aryloxy, arylsulfanyl, aralkyl, aralkyloxy, aralkylsulfanyl, arylalkenyl, arylalkynyl, heteroaryl, heteroaryloxy, heteroarylsulfanyl, heteroaralkyl, (heteroaryl)alkoxy, or (heteroaryl)alkylsulfanyl.

As defined above, when m≧2, two adjacent $R^1$ groups can join together to form a 4- to 8-membered optionally substituted cyclic moiety. That is, the 2-pyridyl ring can fuse with a 4- to 8-membered cyclic moiety to form a moiety such as 7H-[1]pyrindinyl, 6,7-dihydro-5H-[1]pyrindinyl, 5,6,7,8-tetrahydro-quinolinyl, 5,7-dihydro-furo[3,4-b]pyridinyl, or 3,4-dihydro-1H-thiopyrano[4,3-c]pyridinyl. The fused ring moiety can be optionally substituted with one or more substituents such as alkyl (including carboxyalkyl, hydroxyalkyl, and haloalkyl such as trifluoromethyl; see definition of "alkyl" below), alkenyl, alkynyl, cycloalkyl, heterocycloalkyl, alkoxy, aryl, heteroaryl, aryloxy, heteroaryloxy, aralkyloxy, heteroarylalkoxy, aroyl, heteroaroyl, amino, nitro, carboxy, alkoxycarbonyl, alkylcarbonyloxy, aminocarbonyl, alkylcarbonylamino, cycloalkylcarbonylamino, cycloalkylalkylcarbonylamino, arylcarbonylamino, aralkylcarbonylamino, heterocycloalkylcarbonylamino, heterocycloalkyl-alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

Similarly, when n≧2, two adjacent $R^2$ groups can join together to form a 4- to 8-membered optionally substituted cyclic moiety, thereby forming a ring fused with the pyridyl or pyrimidinyl group. Some examples of such a moiety are shown below:

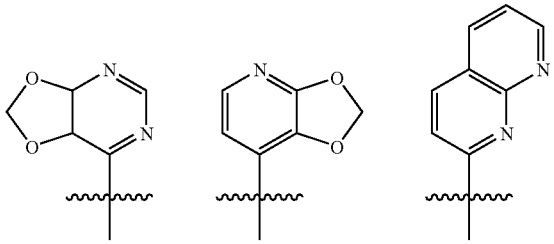

The 4- to 8-membered cyclic moiety formed by two adjacent $R^2$ groups can be optionally substituted with substituents such as alkyl (including carboxyalkyl, hydroxyalkyl, and haloalkyl such as trifluoromethyl; see definition of "alkyl" below), alkenyl, alkynyl, cycloalkyl, heterocycloalkyl, alkoxy, aryl, heteroaryl, aryloxy, heteroaryloxy, aralkyloxy, heteroarylalkoxy, aroyl, heteroaroyl, amino, nitro, carboxy, alkoxycarbonyl, alkylcarbonyloxy, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkylalkyl-carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

In one embodiment, each of $X_1$, $X_2$, $X_3$, and $X_4$ is independently $CR^x$. In one embodiment, each of $X_2$, $X_3$, and $X_4$ is independently —CH—, —C(CH$_3$)—, —C(OH)—, —C(NH$_2$)—, —C(CO—NH$_2$)—, —C(CO—NHOH)—, —C(NH(unsubstituted alkyl))-, —C(NH(aryl))-, —C(NH(aralkyl))-, —C(NH(heteroaryl))-, —C(NH(heteroarylalkyl))-, —C(NH—CO-(unsubstituted alkyl))-, —C(NH—CO-(aryl))-, —C(NH—CO-(heteroaryl))-, —C(NH—CO-(aralkyl))-, —C(NH—CO-(heteroarylalkyl))-, —C(NH—SO$_2$—(unsubstituted alkyl))-, —C(NH—SO$_2$—(aryl))-, —C(NH—SO$_2$—(heteroaryl))-, —C(NH—SO$_2$—(aralkyl))-, —C(NH—SO$_2$-(heteroarylalkyl))-, —C(NH—SO$_2$—NH(unsubstituted alkyl))-, —C(NH—SO$_2$—NH(aryl))-, —C(NH—SO$_2$—NH(heteroaryl))-, —C(NH—SO$_2$—NH(aralkyl))-, —C(NH—SO$_2$—NH(heteroarylalkyl))-, —C(hydroxyalkyl)-, or —C(carboxy)- and $X_1$ is —CH—.

In one embodiment, both $Y_1$ are $Y_2$ are N.

In one embodiment, m is 0, 1, or 2 (e.g., m is 1). In one embodiment, $R^1$ is substituted at the 5-position or the 6-position (i.e., $R^1$ can be mono-substituted at either the 5-position or the 6-position or $R^1$ can be di-substituted at both the 5- and the 6-positions). In one embodiment, $R^1$ is $C_{1-4}$ alkyl, $C_{1-4}$ alkoxy, $C_{1-4}$ alkylthio, halo, amino, aminocarbonyl, or alkoxycarbonyl.

In one embodiment, n is 1 or 2 (e.g., n is 1).

In one embodiment, each $R^1$ is independently unsubstituted alkyl (e.g., 6-methyl, 6-ethyl, 6-n-propyl, or 6-isopropyl), hydroxyalkyl, haloalkyl (e.g., 6-trifluoromethyl), aminoalkyl, aryloxyalkyl, heteroaralkyloxyalkyl, unsubstituted alkenyl (e.g., 6-vinyl), alkoxy, acyl, halo, hydroxy, carboxy, cyano, guanadino, amidino, amino (e.g., —NH$_2$, monoalkylamino, dialkylamino, monoheterocycloalkylamino, monoheteroarylamino, mono(heterocyclylalkyl)amino, mono (aralkyl)amino, or mono(heteroaralkyl)amino), carboxy, mercapto, alkylsulfanyl, alkylsulfinyl alkylsulfonyl, aminocarbonyl (e.g., —CONH$_2$, —CONH(alkyl), or —CO—N(alkyl)$_2$), alkylcarbonylamino (e.g., —NH—CO-alkyl or —N(alkyl)-CO-alkyl), alkoxycarbonyl, alkylcarbonyloxy, alkylsulfonyl, sulfamoyl (e.g., —SO$_2$—NH$_2$, —SO$_2$—NH(alkyl), or —SO$_2$—N(alkyl)$_2$), cycloalkyl (e.g., 6-cyclopropyl), heterocycloalkyl, (heterocycloalkyl)alkyl, heteroaryl, or heteroaralkyl.

In one embodiment, each $R^2$ is independently unsubstituted alkyl, hydroxyalkyl, haloalkyl, aminoalkyl (e.g., aminomethyl), aryloxyalkyl, heteroaralkyloxyalkyl, alkoxy, acyl, halo, hydroxy, carboxy, cyano, guanadino, amidino, —NH$_2$, monoalkylamino, dialkylamino, monocycloalkylamino, monoheterocycloalkylamino (e.g., —NH-piperidinyl or —NH-morpholino), monoheteroarylamino (e.g., —NH-tetrazolyl, —NH-pyrazolyl, or —NH-imidazolyl), mono((heterocycloalkyl)alkyl)amino (e.g., —NH—(CH$_2$)$_{1-3}$-piperidinyl or —NH—(CH$_2$)$_{1-3}$-morpholino), mono(heteroaralkyl)amino (e.g., —NH—(CH$_2$)$_{1-3}$-tetrazolyl, —NH—(CH$_2$)$_{1-3}$-pyrazolyl, or —NH—(CH$_2$)$_{1-3}$-imidazolyl), —N(alkyl)(cycloalkyl), mercapto, alkylsulfanyl, alkylsulfinyl, alkylsulfonyl, —CONH$_2$, —CONH(alkyl), —CO—N(alkyl)$_2$, —NH—CO-alkyl, —N(alkyl)-CO-alkyl, —CO$_2$-alkyl, —O—CO-alkyl, —SO$_2$—NH$_2$, —SO$_2$—NH(alkyl), —SO$_2$—N(alkyl)$_2$, —NH—SO$_2$-alkyl, —N(alkyl)-SO$_2$-alkyl, —NH—CO—NH(alkyl), —N(alkyl)-CO—NH(alkyl), —NH—SO$_2$—NH(alkyl), —N(alkyl)-SO$_2$—NH(alkyl), heterocycloalkyl, or heteroaryl (e.g., imidazolyl, pyrazolyl, tetrazolyl, or pyridyl). For example, $R^2$ is substituted at the 3-position and is guanadino, amidino, —NH$_2$, monoalkylamino, dialkylamino, monocycloalkylamino, monoheterocycloalkylamino, monoheteroarylamino, mono((heterocycloalkyl)alkyl)amino, mono(heteroaralkyl)amino, —NH—CO—NH(alkyl), —N(alkyl)-CO—NH(alkyl), —NH—SO$_2$—NH(alkyl), —N(alkyl)-SO$_2$—NH(alkyl), heterocycloalkyl, or heteroaryl.

In one embodiment, each $R^x$ is independently hydrogen, unsubstituted alkyl, hydroxyalkyl (e.g., hydroxy-C$_{1-4}$ alkyl such as hydroxyethyl), haloalkyl (e.g., trifluoromethyl), aminoalkyl, aryloxyalkyl, heteroaralkyloxyalkyl, alkoxy (e.g., C$_{1-4}$ alkoxy such as methoxy or C$_{1-4}$ haloalkoxy such as —OCF$_3$), halo (e.g., chloro or bromo), hydroxy, carboxy, cyano, guanadino, amidino, amino (e.g., —NH$_2$, —NH(alkyl), —N(alkyl)$_2$, —NH(heterocycloalkyl), —NH(heteroaryl), —NH(heterocycloalkyl-alkyl), —NH(aralkyl), or —NH(heteroaralkyl)), carboxy, (heteroaryl)acyl, aminocarbonyl (e.g., —CO—NH$_2$, —CO—NH—(CH$_2$)$_{0-3}$—COOH, —CO—NH—(CH$_2$)$_3$—OH, —CO—NH—(CH$_2$)$_{0-3}$-heteroaryl (e.g., —CO—NH—(CH$_2$)$_{0-3}$-tetrazolyl, —CO—NH—(CH$_2$)$_{0-3}$-pyrazolyl, or —CO—NH—(CH$_2$)$_{0-3}$-imidazolyl), —CO—NH—(CH$_2$)$_{0-3}$-heterocycloalkyl (e.g., —CO—NH—(CH$_2$)$_{0-3}$-piperidinyl or —CO—NH—(CH$_2$)$_{0-3}$-morpholino), or —CO—NH—(CH$_2$)$_{0-3}$-aryl (e.g., —CO—NH—(CH$_2$)$_{0-3}$-phenyl), heteroarylcarbonylamino, (heterocycloalkyl)alkoxy, (heteroaryl)alkoxy, (heteroaryl)alkylsulfanyl, heterocycloalkyl (e.g., morpholino, pyrazinyl, or piperidinyl), (heterocycloalkyl)alkyl (e.g., morpholino-C$_{1-4}$ alkyl, pyrazinyl-C$_{1-4}$ alkyl, or piperidinyl-C$_{1-4}$ alkyl), heteroaryl (e.g., imidazolyl, pyrazolyl, tetrazolyl, or pyridyl), or heteroaralkyl (e.g., imidazolyl-C$_{1-4}$ alkyl, pyrazolyl-C$_{1-4}$ alkyl, tetrazolyl-C$_{1-4}$ alkyl, or pyridyl-C$_{1-4}$ alkyl). Some examples of —NH(alkyl) are —NH(haloalkyl) (e.g., —NHCF$_3$), —NH(carboxyalkyl) (e.g., —NH(CH$_2$)$_{1-3}$COOH), and —NH(hydroxyalkyl) (e.g., —NH(CH$_2$)$_{1-3}$OH). Some examples of —NH(heteroaryl) are —NH(tetrazolyl), —NH(pyrazolyl), and —NH(imidazolyl). Some examples of —NH(heterocycloalkyl-alkyl) are —NH(piperazinylalkyl) (e.g., —NH(CH$_2$)$_{1-3}$-piperizine) and —NH(morpholino-alkyl) (e.g., —NH(CH$_2$)$_{1-3}$-morpholine). Some examples of —NH(heteroaralkyl) are —NH(tetrazolylalkyl) (e.g., —NH(CH$_2$)$_{1-3}$-tetrazole), —NH(pyrazolylalkyl) (e.g., —NH(CH$_2$)$_{0-3}$-pyrazole), and —NH(imidazolyl-alkyl) (e.g., —NH(CH$_2$)$_{0-3}$-imidazole).

In one embodiment, $R^y$ is hydrogen, unsubstituted alkyl, hydroxyalkyl, haloalkyl (e.g., trifluoromethyl), aminoalkyl, aryloxyalkyl, heteroaralkyloxyalkyl, alkoxy, halo, hydroxy, carboxy, cyano, guanadino, amidino, amino (e.g., —NH$_2$, —NH(alkyl), —N(alkyl)$_2$, —NH(cycloalkyl), —NH(heterocycloalkyl), —NH(heteroaryl), —NH(heterocycloalkylalkyl), —NH(aralkyl), or —NH(heteroaralkyl)), carboxy, (heteroaryl)acyl, aminocarbonyl, heteroarylcarbonylamino, (heterocycloalkyl)alkoxy, (heteroaryl)alkoxy, (heteroaryl)alkylsulfanyl, heterocycloalkyl, (heterocycloalkyl)alkyl, heteroaryl, or heteroaralkyl.

In one embodiment, $X_1$ is N. For example, $X_1$ is N and each of $X_2$, $X_3$, and $X_4$ is independently $CR^x$.

In one embodiment, $X_2$ is N. For example, $X_2$ is N and each of $X_1$, $X_3$, and $X_4$ is independently $CR^x$.

In one embodiment, $X_3$ is N. For example, $X_3$ is N and each of $X_1$, $X_2$, and $X_4$ is independently $CR^x$.

In one embodiment, $X_4$ is N. For example, $X_4$ is N and each of $X_1$, $X_2$, and $X_3$ is independently $CR^x$.

Some examples of a compound of formula (I) are 4-(2-pyridin-2-yl-pyrazolo[1,5-a]pyridin-3-yl)-pyrimidin-2-ylamine, 4-[2-(6-methyl-pyridin-2-yl)-pyrazolo[1,5-a]pyridin-3-yl]-pyrimidin-2-ylamine, 2-(6-methyl-pyridin-2-yl)-3-(2-methylsulfanyl-pyrimidin-4-yl)-pyrazolo[1,5-a]pyridine, 4-[2-(6-chloro-pyridin-2-yl)-pyrazolo[1,5-c]pyrimidin-3-yl]-pyrimidin-2-ylamine, 2-(6-methyl-pyridin-2-yl)-3-(2-morpholin-4-yl-pyrimidin-4-yl)-pyrazolo[1,5-c]pyrimidine, 4-[2-(6-methyl-pyridin-2-yl)-pyrazolo[1,5-a]pyrazin-3-yl]-pyrimidin-2-ylamine, 4-[2-(6-methyl-pyridin-2-yl)-pyrazolo[1,5-a]pyrimidin-3-yl]-pyrimidin-2-ylamine, and 4-[2-(6-methyl-pyridin-2-yl)-pyrazolo[1,5-c]pyrimidin-3-yl]-pyrimidin-2-ylamine.

An N-oxide derivative or a pharmaceutically acceptable salt of each of the compounds of formula (I) is also within the scope of this invention. For example, a nitrogen ring atom of the imidazole core ring or a nitrogen-containing heterocyclyl substituent can form an oxide in the presence of a suitable oxidizing agent such as m-chloroperbenzoic acid or $H_2O_2$.

A compound of formula (I) that is acidic in nature (e.g., having a carboxyl or phenolic hydroxyl group) can form a pharmaceutically acceptable salt such as a sodium, potassium, calcium, or gold salt. Also within the scope of the invention are salts formed with pharmaceutically acceptable amines such as ammonia, alkyl amines, hydroxyalkylamines, and N-methylglycamine. A compound of formula (I) can be treated with an acid to form acid addition salts. Examples of such an acid include hydrochloric acid, hydrobromic acid, hydroiodic acid, sulfuric acid, methanesulfonic acid, phosphoric acid, p-bromophenyl-sulfonic acid, carbonic acid, succinic acid, citric acid, benzoic acid, oxalic acid, malonic acid, salicylic acid, malic acid, fumaric acid, ascorbic acid, maleic acid, acetic acid, and other mineral and organic acids well known to a skilled person in the art. The acid addition salts can be prepared by treating a compound of formula (I) in its free base form with a sufficient amount of an acid (e.g., hydrochloric acid) to produce an acid addition salt (e.g., a hydrochloride salt). The acid addition salt can be converted back to its free base form by treating the salt with a suitable dilute aqueous basic solution (e.g., sodium hydroxide, sodium bicarbonate, potassium carbonate, or ammonia). Compounds of formula (I) can also be, e.g., in a form of achiral compounds, racemic mixtures, optically active compounds, pure diastereomers, or a mixture of diastereomers.

Compounds of formula (I) exhibit surprisingly high affinity to the TGFβ family type I receptors, Alk 5 and/or Alk 4, e.g., with an $IC_{50}$ value of less than 10 µM under conditions as described in Examples 2 and 3 below. Some compounds of formula (I) exhibit an $IC_{50}$ value of below 0.1 µM.

Compounds of formula (I) can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

In another aspect, the present invention features a pharmaceutical composition comprising a compound of formula (I) (or a combination of two or more compounds of formula (I)) and a pharmaceutically acceptable carrier. Also included in the present invention is a medicament composition including any of the compounds of formula (I), alone or in a combination, together with a suitable excipient.

In a further aspect, the invention features a method of inhibiting the TGFβ family type I receptors, Alk 5 and/or Alk 4 (e.g., with an $IC_{50}$ value of less than 10 µM; preferably, less than 1 µM; more preferably, less than 0.1 µM) in a cell, including the step of contacting the cell with an effective amount of one or more compounds of formula (I). Also with the scope of the invention is a method of inhibiting the TGFβ and/or activin signaling pathway in a cell or in a subject (e.g., a mammal such as human), including the step of contacting the cell with or administering to the subject an effective amount of one or more of a compound of formula (I).

Also within the scope of the present invention is a method of treating a subject or preventing a subject from suffering a condition characterized by or resulted from an elevated level of TGFβ and/or activin activity (e.g., from an overexpression of TGFβ). The method includes the step of administering to the subject an effective amount of one or more of a compound of formula (I). The conditions include an accumulation of excess extracellular matrix; a fibrotic condition (e.g., scleroderma, lupus nephritis, connective tissue disease, wound healing, surgical scarring, spinal cord injury, CNS scarring, acute lung injury, idiopathic pulmonary fibrosis, chronic obstructive pulmonary disease, adult respiratory distress syndrome, acute lung injury, drug-induced lung injury, glomerulonephritis, diabetic nephropathy, hypertension-induced nephropathy, hepatic or biliary fibrosis, liver cirrhosis, primary biliary cirrhosis, fatty liver disease, primary sclerosing cholangitis, restenosis, cardiac fibrosis, opthalmic scarring, fibrosclerosis, fibrotic cancers, fibroids, fibroma, fibroadenomas, fibrosarcomas, transplant arteriopathy, and keloid); demyelination of neurons multiple sclerosis; Alzheimer's disease; cerebral angiopathy; and TGFβ-induced metastasis of tumor cells and carcinomas (e.g, squamous cell carcinomas, multiple myeloma, melanoma, glioma, glioblastomas, leukemia, and carcinomas of the lung, breast, ovary, cervix, liver, biliary tract, gastrointestinal tract, pancreas, prostate, and head and neck).

As used herein, an "alkyl" group refers to a saturated aliphatic hydrocarbon group containing 1-8 (e.g., 1-6 or 1-4) carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, n-heptyl, and 2-ethylhexyl. An alkyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, an "alkynyl" group refers to an aliphatic carbon group that contains 2-8 (e.g., 2-6 or 24) carbon atoms and has at least one triple bond. An alkynyl group can be straight or branched. Examples of an alkynyl group include, but are not limited to, propargyl and butynyl. An alkynyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, an "amino" group refers to —$NR^{X}R^{Y}$ wherein each of $R^{X}$ and $R^{Y}$ is independently hydrogen, hydroxyl, alkyl, alkoxy, cycloalkyl, (cycloalkyl)alkyl, aryl, aralkyl, heterocycloalkyl, (heterocycloalkyl)alkyl, heteroaryl, or heteroaralkyl. When the term "amino" is not the terminal group (e.g., alkylcarbonylamino), it is represented by —$NR^{X}$—. $R^{X}$ has the same meaning as defined above.

As used herein, an "aryl" group refers to phenyl, naphthyl, or a benzofused group having 2 to 3 rings. For example, a benzofused group includes phenyl fused with one or two $C_{4-8}$ carbocyclic moieties, e.g., 1,2,3,4-tetrahydronaphthyl, indanyl, or fluorenyl. An aryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl.

As used herein, a "cycloalkyl" group refers to an aliphatic carbocyclic ring of 3-10 (e.g., 4-8) carbon atoms. Examples of cycloalkyl groups include cyclopropyl, cyclopentyl, cyclohexyl, cycloheptyl, adamantyl norbornyl, cubyl, octahydro-indenyl, decahydro-naphthyl, bicyclo[3.2.1]octyl, bicyclo[2.2.2]octyl, bicyclo[3.3.1]nonyl, and bicyclo[3.2.3]nonyl. A "cycloalkenyl" group, as used herein, refers to a non-aromatic carbocyclic ring of 3-10 (e.g., 4-8) carbon atoms having one or more double bond. Examples of cycloalkenyl groups include cyclopentenyl, 1,4-cyclohexa-di-enyl, cycloheptenyl, cyclooctenyl, hexahydro-indenyl, octahydro-naphthyl, bicyclo[2.2.2]octenyl, and bicyclo[3.3.1]nonenyl. A cycloalkyl or cycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, a "heterocycloalkyl" group refers to a 3- to 10-membered (e.g., 4- to 8-membered) saturated ring structure, in which one or more of the ring atoms is a heteroatom, e.g., N, O, or S. Examples of a heterocycloalkyl group include piperidinyl, piperazinyl, tetrahydropyranyl, tetrahydrofuryl, dioxolanyl, oxazolidinyl, isooxazolidinyl, morpholinyl, octahydro-benzofuryl, octahydro-chromenyl, octahydro-thiochromenyl, octahydro-indolyl, octahydro-pyrindinyl, decahydro-quinolinyl, octahydro-benzo[b]thiophenyl, 2-oxa-bicyclo[2.2.2]octyl, 1-aza-bicyclo[2.2.2]octyl, 3-aza-bicyclo[3.2.1]octyl, anad 2,6-dioxa-tricyclo[3.3.1.0$^{3,7}$]nonyl. A "heterocycloalkenyl" group, as used herein, refers to a 3- to 10-membered (e.g., 4- to 8-membered) non-aromatic ring structure having one or more double bonds, and wherein one or more of the ring atoms is a heteroatom, e.g., N, O, or S. A heterocycloalkyl or heterocycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

A "heteroaryl" group, as used herein, refers to a monocyclic, bicyclic, or tricyclic ring structure having 5 to 15 ring atoms wherein one or more of the ring atoms is a heteroatom, e.g., N, O, or S and wherein one ore more rings of the bicyclic or tricyclic ring structure is aromatic. Some examples of heteroaryl are pyridyl, furyl, pyrrolyl, thienyl, thiazolyl, oxazolyl, imidazolyl, indolyl, tetrazolyl, benzofuryl, benzthiazolyl, xanthene, thioxanthene, phenothiazine, dihydroindole, and benzo[1,3]dioxole. A heteroaryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl. A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic moiety" includes cycloalkyl, heterocycloalkyl, cycloalkenyl, heterocycloalkenyl, aryl, or heteroaryl, each of which has been defined previously.

As used herein, an "acyl" group refers to a formyl group or alkyl-C(=O)— where "alkyl" has been defined previously. Acetyl and pivaloyl are examples of acyl groups.

As used herein, a "carbamoyl" group refers to a group having the structure —O—CO—NR$^X$R$^Y$ or —NR$^X$—CO—R$^Z$ wherein R$^X$ and R$^Y$ have been defined above and R$^Z$ is alkyl, cycloalkyl, (cycloalkyl)alkyl, aryl, aralkyl, heterocycloalkyl, (heterocycloalkyl)alkyl, heteroaryl, or heteroaralkyl.

As used herein, a "carboxy" and a "sulfo" group refer to —COOH and —SO$_3$H, respectively.

As used herein, an "alkoxy" group refers to an alkyl-O— group where "alkyl" has been defined previously.

As used herein, a "sulfoxy" group refers to —O—SO—R$^X$ or —SO—O—R$^X$, where R$^X$ has been defined above.

As used herein, a "halogen" or "halo" group refers to fluorine, chlorine, bromine or iodine.

As used herein, a "sulfamoyl" group refers to the structure —SO$_2$—NR$^X$R$^Y$ or —NR$^X$—SO$_2$—R$^Z$ wherein R$^X$, R$^Y$, and R$^Z$ have been defined above.

As used herein, a "sulfamide" group refers to the structure —NR$^X$—S(O)$_2$—NR$^Y$R$^Z$ wherein R$^X$, R$^Y$, and R$^Z$ have been defined above.

As used herein, a "urea" group refers to the structure —NR$^X$—CO—NR$^Y$R$^Z$ and a "thiourea" group refers to the structure —NR$^X$—CS—NR$^Y$R$^Z$. R$^X$, R$^Y$, and R$^Z$ have been defined above.

As used herein, an effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

An antagonist is a molecule that binds to the receptor without activating the receptor. It competes with the endogenous ligand(s) or substrate(s) for binding site(s) on the receptor and, thus inhibits the ability of the receptor to transduce an intracellular signal in response to endogenous ligand binding.

As compounds of formula (I) are antagonists of TGFβ receptor type I (Alk5) and/or activin receptor type I (Alk4), these compounds are useful in inhibiting the consequences of TGFβ and/or activin signal transduction such as the production of extracellular matrix (e.g., collagen and fibronectin), the differentiation of stromal cells to myofibroblasts, and the stimulation of and migration of inflammatory cells. Thus, compounds of formula (I) inhibit pathological inflammatory and fibrotic responses and possess the therapeutical utility of treating and/or preventing disorders or diseases for which reduction of TGFβ and/or activin activity is desirable (e.g., various types of fibrosis or progressive cancers).

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In addition, the materials, methods, and examples are illustrative only and not intended to be limiting.

Other features and advantages of the invention will be apparent from the following detailed description, and from the claims.

DETAILED DESCRIPTION OF THE INVENTION

In general, the invention features compounds of formula (I), which exhibit surprisingly high affinity for the TGFβ family type I receptors, Alk 5 and/or Alk 4.

Synthesis of Compounds of Formula (I)

Compounds of formula (I) may be prepared by a number of known methods from commercially available or known starting materials. In one method, compounds of formula (I) are prepared according to Scheme 1 below. Specifically, a compound of formula (II) (where $X_1$, $X_2$, $X_3$, and $X_4$ have each been defined before) can undergo dipolar cycloaddition with an acetylene of formula (I) in an inert solvent (e.g., $CH_2Cl_2$) with an appropriate base (e.g., KOH) to form an intermediate, a compound of formula (IV) as shown below. This intermediate can then react with an amine of formula (V) where $R^A$ is a lower alkyl (e.g., $C_{1-4}$ alkyl such as methyl) and $R^B$ is an appropriate leaving group (e.g., $C_{1-4}$ alkoxy such as ethoxy) to form a further intermediate, a compound of formula (VI). Further reaction of this intermediate with reagents such as an optionally substituted guanidine (wherein R shown below in Scheme 1 can be hydrogen, alkyl, cycloalkyl, aryl, heterocycloalkyl, or heteroaryl) or thiourea leads to compounds of formula (I).

Alternatively, the intermediate compound of formula (IV) can be alkylated by reacting with diethoxy ketone in a polar solvent (e.g., dioxane) at an elevated temperature (e.g., 90° C.) to result in a further intermediate, a compound of formula (VII). This intermediate can then react with a reagent such as guanidine carbonate at an elevated temperature (e.g., 100° C.) to form a compound of formula (I) with an aminopyrimidinone substituent. This compound of formula (I) can be further derivatized to other compounds of formula (I) (e.g., by converting the aminopyrimidinone substituent to a diaminopyrimidine substituent as shown in Scheme 1).

Scheme 1

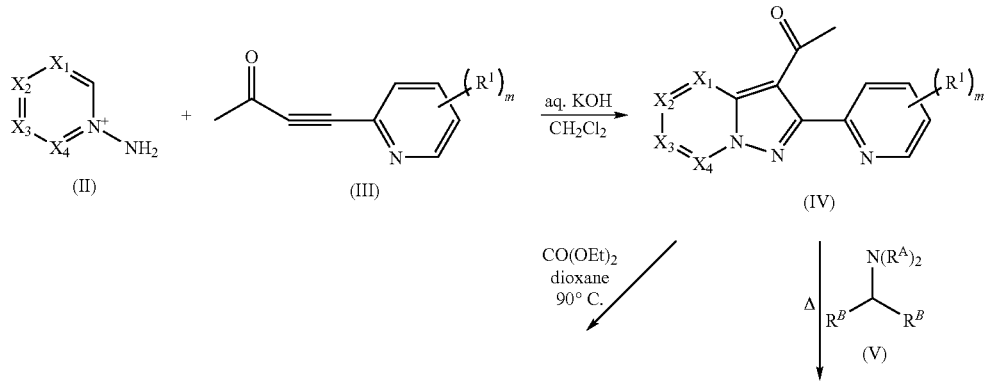

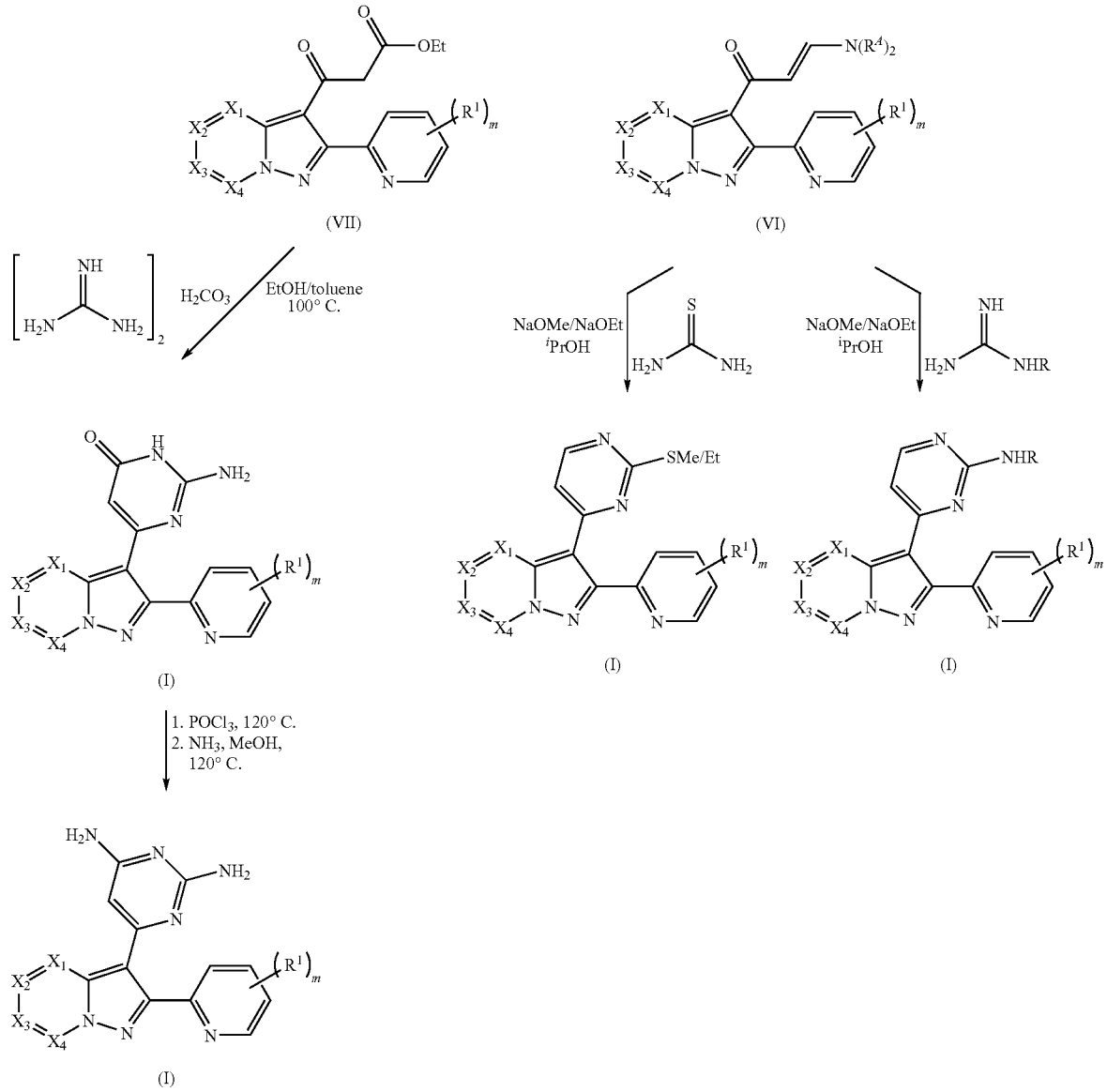
Some other methods for derivatizing compounds of formula (I) are shown in Scheme 2 below.
Scheme 2
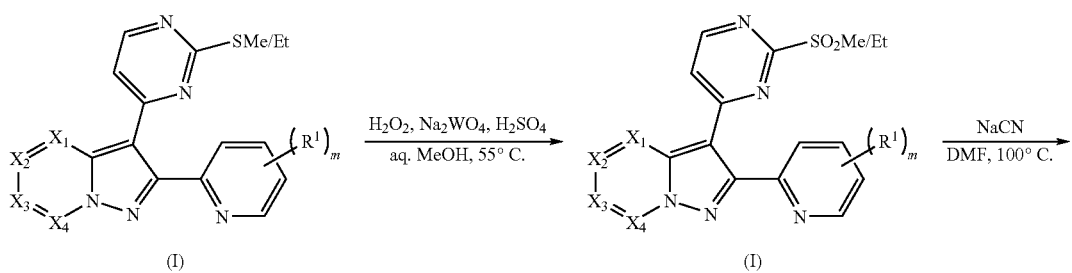

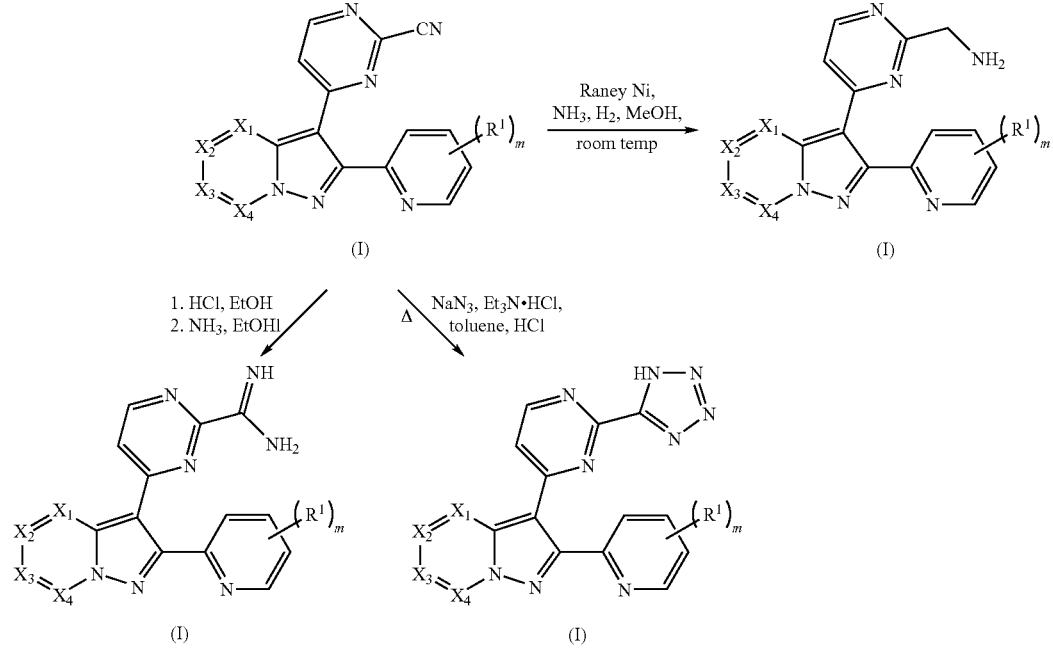

Scheme 3 shows a yet another method for preparing compounds of formula (I). Specifically, a compound of formula (II) can cyclize with an acetylene of formula (VIII) to form an intermediate compound of formula (IX). Reaction of this intermediate with NaOH, followed by a brominating agent (N-bromosuccinimide) yields a compound of formula (X). Further reaction of a compound of formula (X) with either reagent of formula (XI) or formula (XII) produces compounds of formula (I). For references, see Stille, *Angew. Chem. In. Ed. Engl.* 25, 508 (1996) and Suzuki et al., *Synth. Commun.* 11, 513 (1981).

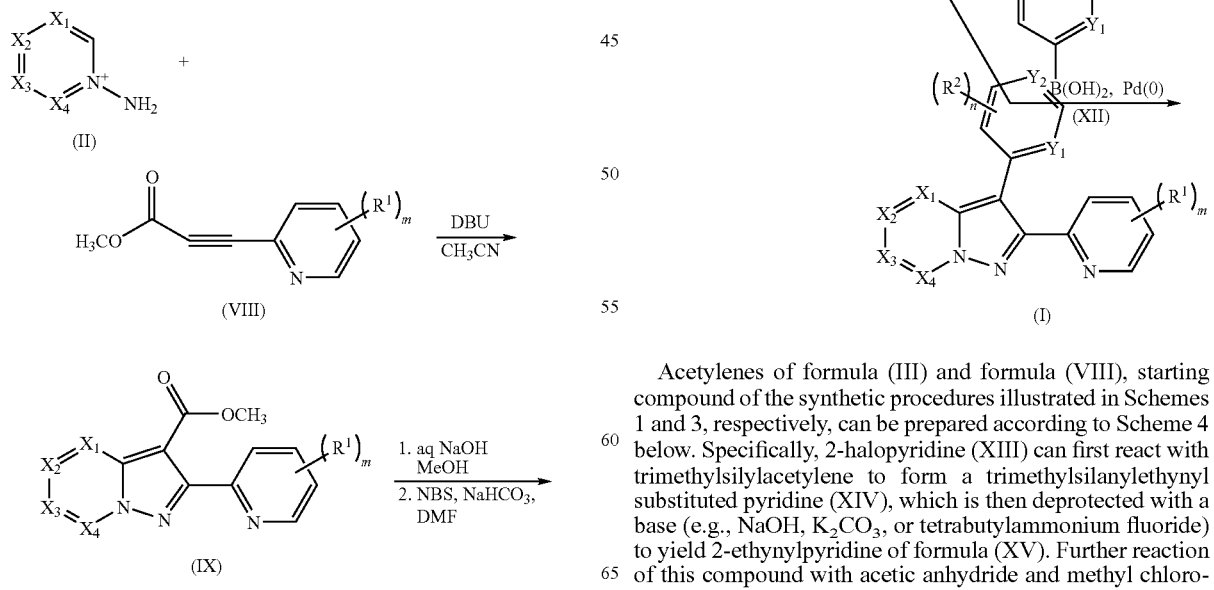

Acetylenes of formula (III) and formula (VIII), starting compound of the synthetic procedures illustrated in Schemes 1 and 3, respectively, can be prepared according to Scheme 4 below. Specifically, 2-halopyridine (XIII) can first react with trimethylsilylacetylene to form a trimethylsilanylethynyl substituted pyridine (XIV), which is then deprotected with a base (e.g., NaOH, $K_2CO_3$, or tetrabutylammonium fluoride) to yield 2-ethynylpyridine of formula (XV). Further reaction of this compound with acetic anhydride and methyl chloroformate produces a compound of formula (III) and formula (VIII), respectively.

Scheme 4

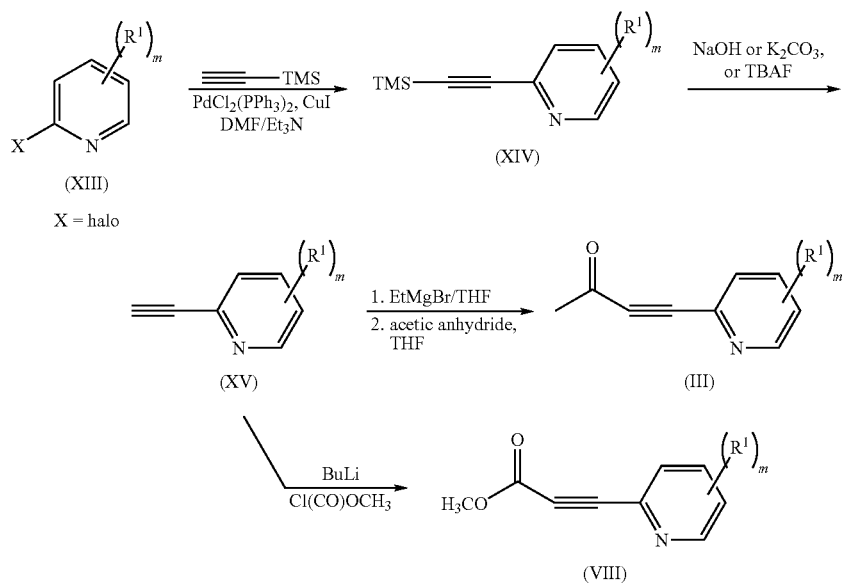

Still further, compounds of formula (I) can be prepared according to Scheme 5 below. Specifically, a diaryl acetylene of formula (XVI) or a ketone of formula (XVII) can cyclize with an aminating agent (e.g., O-(mesitylsulfonyl)-hydroxylamine) to yield a compound of formula (XVIII), which can be brominated (e.g., by using N-bromosuccinimide) to form a compound of formula (X). Further reaction of a compound of formula (X) with either reagent of formula (XI) or formula (XII) produces compounds of formula (I).

Scheme 5

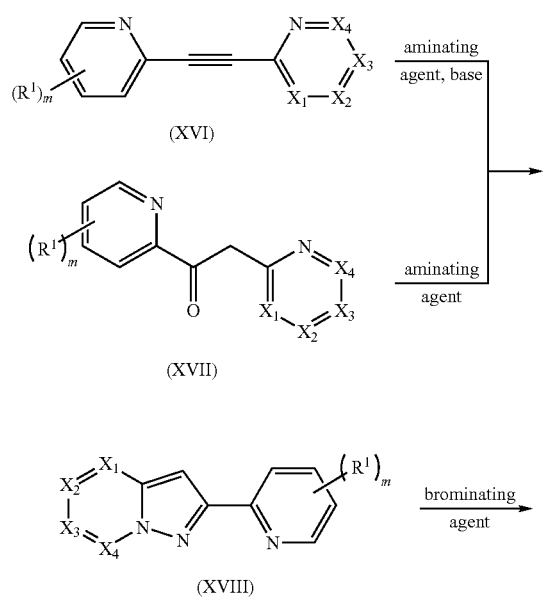

-continued

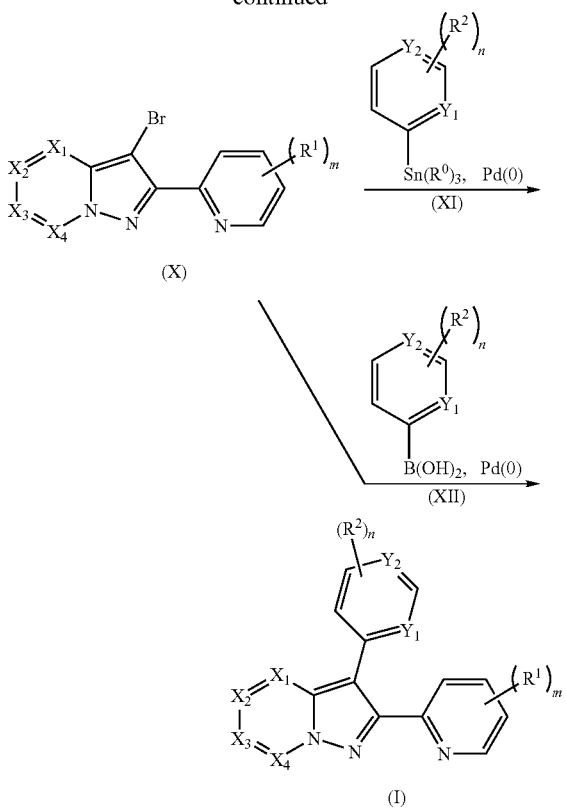

Starting compounds of formula (XVII) can be prepared according to methods analogous to that illustrated in Scheme 4 above, e.g., by coupling an appropriate pyridyl acetylene with 2-halopyridine. For reference, see Yamanake et al., *Chem. Pharm. Bull.* 1890 (1988). Compounds of formula (XVII) can also be prepared according to known methods, e.g., see Cassity et al., *J. Org. Chem.* 2286 (1978).

In addition to Scheme 2, a compound of formula (I) can be modified to other compounds of formula (I) according to Schemes 6 and 7 below. Note that $R^C$ represents alkyl, cycloalkyl, (cycloalkyl)alkyl, aryl, aralkyl, heterocycloalkyl, (heterocycloalkyl)alkyl, heteroaryl, or heteroaralkyl.

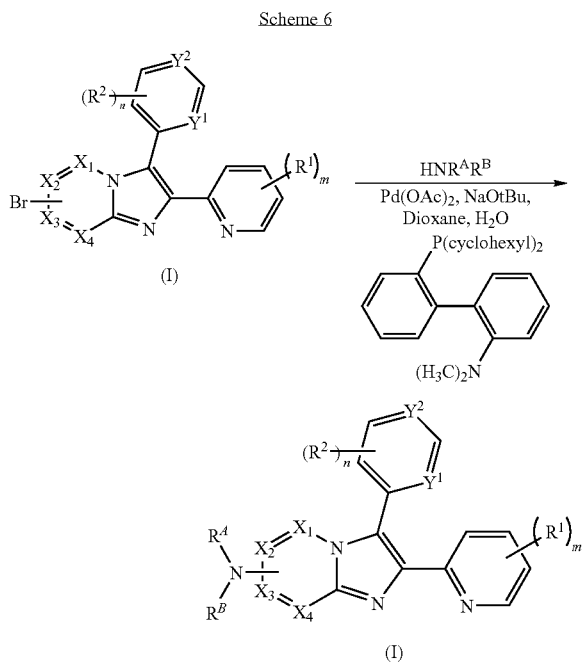

Scheme 6

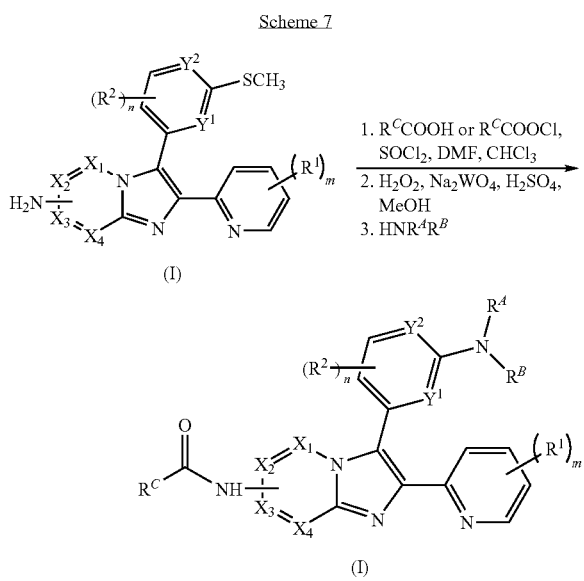

Scheme 7

As will be obvious to a skilled person in the art, some intermediates may need to be protected before undergoing synthetic steps as described above. For suitable protecting groups, see, e.g., T. W. Greene, *Protective Groups in Organic Synthesis*, John Wiley & Sons, Inc., New York (1981).

Uses of Compounds of Formula (I)

As discussed above, hyperactivity of the TGFβ family signaling pathways can result in excess deposition of extracellular matrix and increased inflammatory responses, which can then lead to fibrosis in tissues and organs (e.g., lung, kidney, and liver) and ultimately result in organ failure. See, e.g., Border, W. A. and Ruoslahti E. *J. Clin. Invest.* 90: 1-7 (1992) and Border, W. A and Noble, N. A. *N. Engl. J. Med.* 331: 1286-1292 (1994). Studies have been shown that the expression of TGFβ and/or activin mRNA and the level of TGFβ and/or activin are increased in patients suffering from various fibrotic disorders, e.g., fibrotic kidney diseases, alcohol-induced and autoimmune hepatic fibrosis, myelofibrosis, bleomycin-induced pulmonary fibrosis, and idiopathic pulmonary fibrosis.

Compounds of formula (I), which are antagonists of the TGFβ family type I receptors, Alk 5 and/or Alk 4, and inhibit TGFβ and/or activin signaling pathway, are therefore useful for treating and/or preventing fibrotic disorders or diseases mediated by an increased level of TGFβ and/or activin activity. As used herein, a compound inhibits the TGFβ family signaling pathway when it binds (e.g., with an $IC_{50}$ value of less than 10 μM; preferably, less than 1 μM; more preferably, less than 0.1 μM) to a receptor of the pathway (e.g., Alk 5 and/or Alk 4), thereby competing with the endogenous ligand(s) or substrate(s) for binding site(s) on the receptor and reducing the ability of the receptor to transduce an intracellular signal in response to the endogenous ligand or substrate binding. The aforementioned disorders or diseases include any conditions (a) marked by the presence of an abnormally high level of TGFβ and/or activin; and/or (b) an excess accumulation of extracellular matrix; and/or (c) an increased number and synthetic activity of myofibroblasts. These disorders or diseases include, but are not limited to, fibrotic conditions such as scleroderma, idiopathic pulmonary fibrosis, glomerulonephritis, diabetic nephropathy, lupus nephritis, hypertension-induced nephropathy, ocular or corneal scarring, hepatic or biliary fibrosis, acute lung injury, pulmonary fibrosis, post-infarction cardiac fibrosis, fibrosclerosis, fibrotic cancers, fibroids, fibroma, fibroadenomas, and fibrosarcomas. Other fibrotic conditions for which preventive treatment with compounds of formula (I) can have therapeutic utility include radiation therapy-induced fibrosis, chemotherapy-induced fibrosis, surgically induced scarring including surgical adhesions, laminectomy, and coronary restenosis.

Increased TGFβ activity is also found to manifest in patients with progressive cancers. Studies have shown that in late stages of various cancers, both the tumor cells and the stromal cells within the tumors generally overexpress TGFβ. This leads to stimulation of angiogenesis and cell motility, suppression of the immune system, and increased interaction of tumor cells with the extracellular matrix. See, e.g., Hojo, M. et al., *Nature* 397: 530-534 (1999). As a result, the tumors cells become more invasive and metastasize to distant organs. See, e.g., Maehara, Y. et al., *J. Clin. Oncol.* 17: 607-614 (1999) and Picon, A. et al., *Cancer Epidemiol. Biomarkers Prev.* 7: 497-504 (1998). Thus, compounds of formula (I), which are antagonists of the TGFβ type I receptor and inhibit TGFβ signaling pathway, are also useful for treating and/or preventing various late stage cancers which overexpress TGFβ. Such late stage cancers include carcinomas of the lung, breast, liver, biliary tract, gastrointestinal tract, head and neck, pancreas, prostate, cervix as well as multiple myeloma, melanoma, glioma, and glioblastomas.

Importantly, it should be pointed out that because of the chronic and in some cases localized nature of disorders or diseases mediated by overexpression of TGFβ and/or activin (e.g., fibrosis or cancers), small molecule treatments (such as treatment disclosed in the present invention) are favored for long-term treatment.

Not only are compounds of formula (I) useful in treating disorders or diseases mediated by high levels of TGFβ and/or activin activity, these compounds can also be used to prevent the same disorders or diseases. It is known that polymorphisms leading to increased TGFβ and/or activin production have been associated with fibrosis and hypertension. Indeed, high serum TGFβ levels are correlated with the development of fibrosis in patients with breast cancer who have received radiation therapy, chronic graft-versus-host-disease, idiopathic interstitial pneumonitis, veno-occlusive disease in transplant recipients, and peritoneal fibrosis in patients undergoing continuous ambulatory peritoneal dialysis. Thus, the levels of TGFβ and/or activin in serum and of TGFβ and/or activin mRNA in tissue can be measured and used as diagnostic or prognostic markers for disorders or diseases mediated by overexpression of TGFβ and/or activin, and polymorphisms in the gene for TGFβ that determine the production of TGFβ and/or activin can also be used in predicting susceptibility to disorders or diseases. See, e.g., Blobe, G. C. et al., *N. Engl. J. Med.* 342(18): 1350-1358 (2000); Matsuse, T. et al., *Am. J. Respir. Cell Mol. Biol.* 13: 17-24 (1995); Inoue, S. et al., *Biochem. Biophys. Res. Comm.* 205: 441-448 (1994); Matsuse, T. et al., *Am. J. Pathol.* 148: 707-713 (1996); De Bleser et al., *Hepatology* 26: 905-912 (1997); Pawlowski, J. E., et al., *J. Clin. Invest.* 100: 639-648 (1997); and Sugiyama, M. et al., *Gastroenterology* 114: 550-558 (1998).

Administration of Compounds of Formula (I)

As defined above, an effective amount is the amount which is required to confer a therapeutic effect on the treated patient. For a compound of formula (I), an effective amount can range from about 1 mg/kg to about 150 mg/kg (e.g., from about 1 mg/kg to about 100 mg/kg). Effective doses will also vary, as recognized by those skilled in the art, dependant on route of administration, excipient usage, and the possibility of co-usage with other therapeutic treatments including use of other therapeutic agents and/or radiation therapy.

Compounds of formula (I) can be administered in any manner suitable for the administration of pharmaceutical compounds, including, but not limited to, pills, tablets, capsules, aerosols, suppositories, liquid formulations for ingestion or injection or for use as eye or ear drops, dietary supplements, and topical preparations. The pharmaceutically acceptable compositions include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds. As to route of administration, the compositions can be administered orally, intranasally, transdermally, intradermally, vaginally, intraaurally, intraocularly, buccally, rectally, transmucosally, or via inhalation, implantation (e.g., surgically), or intravenous administration. The compositions can be administered to an animal (e.g., a mammal such as a human, non-human primate, horse, dog, cow, pig, sheep, goat, cat, mouse, rat, guinea pig, rabbit, hamster, gerbil, ferret, lizard, reptile, or bird).

Optionally, compounds of formula (I) can be administered in conjunction with one or more other agents that inhibit the TGFβ signaling pathway or treat the corresponding pathological disorders (e.g., fibrosis or progressive cancers) by way of a different mechanism of action. Examples of these agents include angiotensin converting enzyme inhibitors, non-steroid, steroid anti-inflammatory agents, and chemotherapeutics or radiation, as well as agents that antagonize ligand binding or activation of the TGFβ receptors, e.g., anti-TGFβ, anti-TGFβ receptor antibodies, or antagonists of the TGFβ type II receptors.

The invention will be further described in the following examples, which do not limit the scope of the invention described in the claims.

Synthetic procedures illustrated in Schemes 1 and 2 above were employed in the preparation of the title compound below.

Example 1

4-[2-(6-Methyl-pyridin-2-yl)-pyrazolo[1,5-a]pyridin-3-yl]-pyrimidin-2-ylamine

Synthesis of the title compound is described in parts (a)-(f) below.

(a) 2-methyl-6-trimethylsilanylethynyl-pyridine

Anhydrous triethylamine (45 mL), PdCl$_2$(PPh$_3$)$_2$ (0.48 mmol), and copper(I) iodide (1.45 mmol) were added to a solution of 6-bromo-2-methylpyridine (48.2 mmol) in anhydrous DMF (110 mL). (Trimethylsilyl)acetylene (62.6 mmol) was added dropwise to the resulting orange solution. After stirring overnight at room temperature, the reaction was concentrated in vacuo and diluted with ether (100 mL), hexanes (100 mL) and water (100 mL). This emulsion was filtered through a celite plug, rinsing with ether. The separated organic phase was washed with water (1×), dried (MgSO$_4$) and concentrated in vacuo to give 8.86 g of a dark brown oil identified as 2-methyl-6-trimethylsilanylethynyl-pyridine. $^1$H NMR (CDCl$_3$, 400 MHz): 0.24 (s, 9H), 2.53 (s, 3H), 7.06 (d, J=7.78 Hz, 1H), 7.26 (d, J=7.64 Hz, 1H), 7.50 (dd, J=7.75, 7.74 Hz, 1H); MS (ESP+) 190.09 (M+1).

(b) 2-ethynyl-6-methyl-pyridine

A solution of 2-methyl-6-trimethylsilanylethynyl-pyridine (46.8 mmol) in saturated potassium carbonate/methanol (115 mL) was stirred at RT for 1 h, concentrated in vacuo, dissolved in ether (200 mL), washed with water (2×100 mL), dried (MgSO$_4$) and concentrated in vacuo to give 4.8 g of a dark brown oil identified as 2-ethynyl-6-methyl-pyridine. $^1$H NMR (CDCl$_3$, 400 MHz): 2.53 (s, 3H), 3.10 (s, 1H), 7.10 (d, J=7.81 Hz, 1H), 7.27 (d, J=7.67 Hz, 1H), 7.52 (dd, J=7.75, 7.74 Hz, 1H); MS (+/−) no mol. Ion.

(c) 4-(6-methyl-pyridin-2-yl)-but-3-yn-2-one

A solution of 2-ethynyl-6-methyl-pyridine (41.00 mmol) in anhydrous THF (30 mL) was added dropwise to a solution of 1.0 M ethyl magnesium bromide/THF (61.5 mmol) in anhydrous THF (30 mL) at 0° C. under a nitrogen atmosphere with gas evolution. After stirring for 30 min, the solution was cannulated into a solution of acetic anhydride (82.0 mmol) in anhydrous THF (30 mL) at 0° C. under a nitrogen atmosphere. After a further 45 min. the reaction was quenched with saturated ammonium chloride. After warming to RT, the reaction was diluted with water. The aqueous phase was extracted with ether (2×100 mL). The combined organic phases were washed with saturated ammonium chloride (2×), dried/decolorized (MgSO$_4$/charcoal) and concentrated in vacuo to give 6.54 g of a brown oil identified as 4-(6-methyl-pyridin-2-yl)-but-3-yn-2-one. $^1$H NMR (CDCl$_3$, 400 MHz): 2.45 (s, 3H), 2.56 (s, 3H), 7.19 (d, J=7.83 Hz, 1H), 7.38 (d, J=7.58 Hz, 1H), 7.59 (dd, J=7.76, 7.76 Hz, 1H); MS (+/−) no mol. ion.

(d) 1-[2-(6-methyl-pyridin-2-yl)pyrazolo[1,5-a]pyridin-3-yl]-ethanone

1-Aminopyridinium iodide (82.0 mmol) was added to a solution of 4-(6-methyl-pyridin-2-yl)-but-3-yn-2-one (41.0 mmol) in methylene chloride (60 mL) at RT. After cooling to 0° C., a solution of potassium hydroxide (106.6 mmol) in water (60 mL) was added and the biphasic mixture stirred briskly. After 5 minutes, the reaction was allowed to warm to RT. After 3.5 h, the reaction was diluted with 1:1 methylene chloride/water (120 mL) and the pH was adjusted to 7 with conc. hydrochloric acid. The aqueous phase was extensively extracted with methylene chloride. The combined organic phases were washed with water, dried (MgSO$_4$) and concentrated in vacuo to give a dark brown solid. The solid was dissolved in ethyl acetate (200 mL) and extracted with diluted 1 N hydrochloric acid. The combined aqueous phases were washed with ethyl acetate (1×), adjusted to pH 8 with solid bicarbonate and extracted with ethyl acetate (3×). The combined organic phases were washed with water (1×), brine (1×), dried/decolorized (MgSO$_4$/charcoal) and concentrated in vacuo to give 5.24 g of a tan solid identified as 1-[2-(6-methyl-pyridin-2-yl)-pyrazolo[1,5-a]pyridin-3-yl]-ethanone. $^1$H NMR (CDCl$_3$, 300 MHz): 2.26 (s, 3H), 2.64 (s, 3H), 7.01 (dd, J=6.90, 6.90 Hz, 1H), 7.29 (d, J=7.80 Hz, 1H), 7.47 (dd, J=7.20, 8.70 Hz, 1H), 7.56 (d, J=7.50 Hz, 1H), 7.77 (dd, J=6.60, 7.80 Hz, 1H), 8.40 (d, J=9.00 Hz, 1H), 8.51 (d, J=6.60 Hz, 1H); MS (+/−) no mol. ion.

(e) 3-dimethylamino-1-[2-(6-methyl-pyridin-2-yl)-pyrazolo[1,5-a]pyridin-3-yl]-propenone A solution of 1-[2-(6-methyl-pyridin-2-yl)-pyrazolo[1,5-a]pyridin-3-yl]-ethanone (20.85 mmol) in N,N-dimethylformamide diethylacetal (80 mL) was warmed to 135° C. under a nitrogen atmosphere. After 3 days, the reaction was concentrated in vacuo to a constant mass and identified as 3-dimethylamino-1-[2-(6-methyl-pyridin-2-yl)-pyrazolo[1,5-a]pyridin-3-yl]-propenone. $^1$H NMR (DMSO-d6, 300 MHz: 2.47 (s, 9H), 4.96 (d, J=12.6 Hz, 1H), 7.07 (ddd, J=1.50, 6.90, 6.90 Hz, 1H), 7.30 (d, J=7.78 Hz, 1H), 7.38-7.41 (m, 1H), 7.40 (d, J=12.3 Hz, 1H), 7.44 (d, J=7.50 Hz, 1H), 7.76 (dd, J=7.50, 7.80 Hz, 1H), 8.19 (dd, J=0.90, 8.25 Hz, 1H), 8.71 (dd, 0.90, 6.45 Hz, 1H); MS (ESP+) 307.12 (M+1).

(f) 4-[2-(6-methyl-pyridin-2-yl)-pyrazolo[1,5-a]pyridin-3-yl]-pyrimidin-2-ylamine 21 wt % Sodium ethoxide/ethanol (48.99 mmol) was added to a slurry of guanidine HCl (48.99 mmol) in anhydrous isopropyl alcohol (50 mL). Sodium chloride precipitated immediately. To this suspension was added a solution of 3-dimethylamino-1-[2-(6-methyl-pyridin-2-yl)-pyrazolo[1,5-a]pyridin-3-yl]-propenone (20.85 mmol) in anhydrous isopropyl alcohol (50 mL). The dark suspension was then warmed to reflux overnight. The warm reaction was poured onto ice (130 g), the flask rinsed with water and the rinse added to the ice slurry. The suspension was allowed to stir for 1.5 h, filtered, washed with cold water and air dried to give 2.63 g of a tan solid identified as 4-[2-(6-methyl-pyridin-2-yl)-pyrazolo[1,5-a]pyridin-3-yl]-pyrimidin-2-ylamine. The aqueous mother liquor was concentrated in vacuo, slurried with isopropyl alcohol, filtered, washed with isopropyl alcohol, water and methylene chloride and air dried to give 1.25 g of a tan powder identified as 4-[2-(6-methyl-pyridin-2-yl)-pyrazolo[1,5-a]pyridin-3-yl]-pyrimidin-2-ylamine. The crops were combined for a final reslurry in methylene chloride, solids filtered and air dried to give 3.62 g of tan solid. $^1$H NMR (DMSO-d6, 300 MHz): 2.44 (s, 3H), 6.24 (d, J=5.40 Hz, 1H), 6.50 (br s, 2H), 7.06 (ddd, J=1.40, 6.75, 6.90 Hz, 1H), 7.31 (d, J=7.80 Hz, 1H), 7.41 (ddd, J=1.05, 6.75, 7.80 Hz, 1H), 7.51 (d, J=7.50 Hz, 1H), 7.79 (d, J=7.50, 7.80 Hz, 1H), 7.94 (d, J=5.40 Hz, 1H), 8.55 (dd, J=1.05, 9.15 Hz, 1H), 8.75 (dd, J=0.90, 6.45 Hz, 1H); MS (ESP+) 303.12 (M+1).

The TGFβ or activin inhibitory activity of compounds of formula (I) can be assessed by methods described in the following examples.

Example 2

Cell-Free Assay for Evaluating Inhibition of Autophosphorylation of TGFβ Type I Receptor The serine-threonine kinase activity of TGFβ type I receptor was measured as the autophosphorylation activity of the cytoplasmic domain of the receptor containing an N-terminal poly histidine, TEV cleavage site-tag, e.g., His-TGFβR$^1$. The His-tagged receptor cytoplasmic kinase domains were purified from infected insect cell cultures using the Gibco-BRL FastBac HTb baculovirus expression system.

To a 96-well Nickel FlashPlate (NEN Life Science, Perkin Elmer) was added 20 μl of 1.25 μCi $^{33}$P-ATP/25 μM ATP in assay buffer (50 mM Hepes, 60 mM NaCl, 1 mM MgCl$_2$, 2 mM DTT, 5 mM MnCl$_2$, 2% glycerol, and 0.015% Brij 35). 10 μl of test compounds of formula (I) prepared in 5% DMSO solution were added to the FlashPlate. The assay was then initated with the addition of 20 ul of assay buffer containing 12.5 pmol of His-TGFβRI to each well. Plates were incubated for 30 minutes at room temperature and the reactions were then terminated by a single rinse with TBS. Radiation from each well of the plates was read on a TopCount (Packard). Total binding (no inhibition) was defined as counts measured in the presence of DMSO solution containing with no test compound and non-specific binding was defined as counts measured in the presence of EDTA or non-kinase control.

Alternatively, the reaction performed using the above reagents and incubation conditions but in a microcentrifuge tube was analyzed by separation on a 4-20% SDS-PAGE gel and the incorporation of radiolabel into the 40 kDa His-TGFβRI SDS-PAGE band was quantitated on a Storm Phosphoimager (Molecular Dynamics).

Compounds of formula (I) typically exhibited IC$_{50}$ values of less than 10 μM; some exhibited IC$_{50}$ values of less than 0.1 μM.

Example 3

Cell-Free Assay for Evaluating Inhibition of Activin Type I Receptor Kinase Activity Inhibition of the Activin type I receptor (Alk 4) kinase autophosphorylation activity by test compounds of formula (I) can be determined in a similar manner as described above in Example 2 except that a similarly His-tagged form of Alk 4 (His-Alk 4) was used in place of the His-TGFβRI.

Example 4

Assay for Evaluating Cellular Inhibition of TGFβ Signaling and Cytotoxicity

Biological activity of compounds of formula (I) were determined by measuring their ability to inhibit TGFβ-induced PAI-Luciferase reporter activity in HepG2 cells.

HepG2 cells were stably transfected with the PAI-luciferase reporter grown in DMEM medium containing 10% FBS, penicillin (100 U/ml), streptomycin (100 μg/ml), L-glutamine (2 mM), sodium pyruvate (1 mM), and non essential amino acids (1×). The transfected cells were then plated at a concentration of $2.5 \times 10^4$ cells/well in 96 well plates and starved for 3-6 hours in media with 0.5% FBS at 37° C. in a 5% $CO_2$ incubator. The cells were then stimulated with ligand either 2.5 ng/ml TGFβ in the starvation media containing 1% DMSO and the presence or absence of test compounds of formula (I) and incubated as described above for 24 hours. The media was washed out in the following day and the luciferase reporter activity was detected using the LucLite Luciferase Reporter Gene Assay kit (Packard, cat. no. 6016911) as recommended. The plates were read on a Wallac Microbeta plate reader, the reading of which was used to determine the $IC_{50}$ values of compounds of formula (I) for inhibiting TGFβ-induced PAI-Luciferase reporter activity in HepG2 cells. Compounds of formula (I) typically exhibited $IC_{50}$ values of less 10 uM.

Cytotoxicity was determined using the same cell culture conditions as described above. Specifically, cell viability was determined after overnight incubation with the CytoLite cell viability kit (Packard, cat. no. 6016901). Compounds of formula (I) typically exhibited $LD_{25}$ values greater than 10 μM.

Example 5

Assay for Evaluating Cellular Inhibition of TGFβ Signaling

The cellular inhibition of activin signaling activity by test compounds of formula (I) were determined in a similar manner as described above in Example 4 except that 10 ng/ml of activin is added to serum starved cells in place of the 2.5 ng/ml TGFβ.

Example 6

Assay for TGFβ-Induced Collagen Expression

Preparation of Immortalized Collagen Promotor-Green Fluorescent Protein Cells

Fibroblasts were derived from the skin of adult transgenic mice expressing Green Fluorescent Protein (GFP) under the control of the collagen 1A1 promoter (see Krempen, K. et al., Gene Exp. 8: 151-163 (1999)). Cells were immortalised with a temperature sensitive large T antigen that is active at 33° C. Cells are expanded at 33° C. then transferred to 37° C. so that the large T becomes inactive (see Xu, S. et al., Exp. Cell Res. 220: 407-414 (1995)). Over the course of about 4 days and one split, the cells cease proliferating. Cells are then frozen in aliquots sufficient for a single 96 well plate.

Assay of TGFβ-Induced Collagen-GFP Expression

Cells are thawed, plated in complete DMEM (contains nonessential amino acids, 1 mM sodium pyruvate and 2 mM L-glutamine) with 10% fetal calf serum and incubated overnight at 37° C., 5% $CO_2$. The following day, the cells are trypsinized and transferred into 96 well format with 30,000 cells per well in 50 μl complete DMEM containing 2% fetal calf serum, but without phenol red. The cells are incubated at 37° C. for 3 to 4 hours to allow them to adhere to the plate, solutions containing test compounds of formula (I) are then added to triplicate wells with no TGFβ, as well as triplicate wells with 1 ng/ml TGFβ. DMSO was also added to all of the wells at a final concentration of 0.1%. GFP fluorescence emission at 530 nm following excitation at 485 nm was measured at 48 hours after the addition of solution containing test compounds on a CytoFluor microplate reader (PerSeptive Biosystems). The data are then expressed as the ratio of TGFβ-induced to non-induced for each test sample.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound of the following formula:

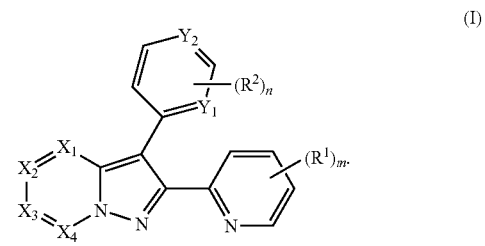

wherein
each of $X_1$, $X_2$, $X_3$, and $X_4$ is independently $CR^x$ or N; provided that only two of $X_1$, $X_2$, $X_3$, and $X_4$ can be N simultaneously;
each of $Y_1$ and $Y_2$ is independently $CR^y$ or N; provided that at least one of $Y_1$ and $Y_2$ must be N;
each $R^1$ is independently alkyl, alkenyl, alkynyl, alkoxy, acyl, halo, hydroxy, amino, nitro, cyano, guanadino, amidino, carboxy, sulfo, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaryl;
each $R^2$ is independently alkyl, alkenyl, alkynyl, acyl, halo, hydroxy, —$NH_2$, —NH(alkyl), —N(alkyl)$_2$, —NH(cycloalkyl), —N(alkyl)(cycloalkyl), —NH(heterocycloalkyl), —NH(heteroaryl), —NH-alkyl-heterocycloalkyl, —NH-alkyl-heteroaryl, —NH(aralkyl), cycloalkyl, (cycloalkyl)alkyl, aryl, aralkyl, aroyl, heterocycloalkyl, (heterocycloalkyl)alkyl, heteroaryl, heteroaralkyl, heteroaroyl, nitro, cyano, guanadino, amidino, carboxy, sulfo, mercapto, alkoxy, cycloalkyloxy, cycloalkyl-alkoxy, aryloxy, arylalkoxy, heterocycloalkyloxy, (heterocycloalkyl)alkoxy, heteroaryloxy, heteroarylalkoxy, alkylsulfanyl, cycloalkylsulfanyl, (cycloalkyl)alkylsulfanyl, arylsulfanyl, aralkylsulfanyl, heterocycloalkylsulfanyl, (heterocycloalkyl)alkylsulfanyl, heteroarylsulfanyl, heteroarylalkylsulfanyl, alkylsulfinyl, alkylsulfonyl, aminocarbonyl, aminosulfonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, alkoxycarbonylaminoalkylamino, (heteroaryl)arylcarbonylaminoalkylamino, heteroaralkylcarbonylaminoalkylamino, (heteroaryl)arylsulfonylaminoalkylcarbonylaminoalkylamino, arylsulfonylaminoalkylamino, alkoxycarbonyl, alkylcarbonyloxy, urea, thiourea, sulfamoyl, sulfamide, or carbamoyl;

m is 0, 1, 2, 3, or 4; provided that when m≧2, two adjacent $R^1$ groups can join together to form a 4- to 8-membered optionally substituted cyclic moiety;

n is 0, 1, 2, or 3; provided that when n≧2 two adjacent $R^2$ groups can join together to form a 4- to 8-membered optionally substituted cyclic moiety; and each of $R^x$ and $R^y$ is independently hydrogen, alkyl, alkenyl, alkynyl, alkoxy, acyl, halo, hydroxy, amino, nitro, cyano, guanadino, amidino, carboxy, sulfo, mercapto, alkylsulfanyl, alkylsulfinyl, alkylsulfonyl, cycloalkylcarbonyl, (cycloalkyl)alkylcarbonyl, aroyl, aralkylcarbonyl, heterocycloalkylcarbonyl, (heterocycloalkyl)acyl, heteroaroyl, (heteroaryl)acyl, aminocarbonyl, alkylcarbonylamino, (amino)aminocarbonyl, alkylsulfonylaminocarbonyl, alkylsulfonylamino, cycloalkylcarbonylamino, cycloalkylsulfonylamino, (cycloalkyl)alkylcarbonylamino, (cycloalkyl)alkylsulfonylamino, arylcarbonylamino, arylsulfonylamino, aralkylcarbonylamino, aralkylsulfonylamino, (heterocycloalkyl)carbonylamino, (heterocycloalkyl)sulfonylamino, (heterocycloalkyl)alkylcarbonylamino, (heterocycloalkyl)alkylsulfonylamino, heteroarylcarbonylamino, heteroarylsulfonylamino, heteroaralkylcarbonylamino, heteroaralkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, (cycloalkyl)alkyl, (cycloalkyl)alkoxy, (cycloalkyl)alkylsulfanyl, heterocycloalkyl, heterocycloalkyloxy, heterocycloalkylsulfanyl, (heterocycloalkyl)alkyl, (heterocycloalkyl)alkoxy, (heterocycloalkyl)alkylsulfanyl, aryl, aryloxy, arylsulfanyl, aralkyl, aralkyloxy, aralkylsulfanyl, arylalkenyl, arylalkynyl, heteroaryl, heteroaryloxy, heteroarylsulfanyl, heteroaralkyl, (heteroaryl)alkoxy, or (heteroaryl)alkylsulfanyl;

or a pharmaceutically acceptable salt thereof.

2. A pharmaceutical composition comprising a compound of claim 1 and a pharmaceutically acceptable carrier.

3. The compound of claim 1, wherein each of $X_1$, $X_2$, $X_3$, and $X_4$ is independently $CR^x$,
each $R^x$ is independently hydrogen.

4. The compound of claim 3, wherein
m is 0, 1 or 2.

5. The compound of claim 4, wherein
both $Y_1$ and $Y_2$ are N.

6. The compound of claim 5 wherein
each $R^1$ is independently unsubstituted alkyl, hydroxyalkyl, haloalkyl, aminoalkyl, aryloxyalkyl, heteroaralkyloxyalkyl, unsubstituted alkenyl, alkoxy, acyl, halo, hydroxy, carboxy, cyano, guanadino, amidino, —$NH_2$, monoalkylamino, diallylamino, monocycloalkylamino, monoheterocycloalkylamino, monoheteroarylamino, mono(heterocyclylalkyl)amino, mono(aralkyl)amino, mono(heteroaralkyl)amino, —N(alkyl)(cycloalkyl), mercapto, alkylsulfanyl, arylsulfinyl, alkylsulfonyl, —$CONH_2$, —CONH(alkyl), —CO—N(alkyl)$_2$, —NH—CO-alkyl, —N(alkyl)-CO-alkyl, —$CO_2$-alkyl, —O—CO-alkyl, —SO—$NH_2$, —$SO_2$—NH(alkyl), —$SO_2$—N(alkyl)$_2$, cycloalkyl, heterocycloalkyl, or heteroaryl.

7. The compound of claim 6,
wherein n is 1 or 2 and $R^2$ is independently and each $R^2$ is independently unsubstituted alkyl, hydroxyalkyl, haloalkyl, aminoalkyl, aryloxyalkyl, heteroaralkyloxyalkyl, alkoxy, acyl, halo, hydroxy, carboxy, cyano, guanadino, amidino, —$NH_2$, monoalkylamino, dialkylamino, monocycloalkylamino, monoheterocycloalkylamino, monoheteroaryl-amino, mono((heterocycloalkyl)alkyl)amino, mono(heteroaralkyl)amino, —N(alkyl)(cycloalkyl), mercapto, alkylsulfanyl, alkylsulfinyl, alkylsulfonyl, —$CONH_2$, —CONH(alkyl), —CO—N(alkyl)$_2$, —NH—CO-alkyl, —N(alkyl)-CO-alkyl, —$CO_2$-alkyl, —O—CO-alkyl, —$SO_2$—$NH_2$, —$SO_2$—NH(alkyl), —$SO_2$—N(alkyl)$_2$, —NH—$SO_2$-alkyl, —N(alkyl)-$SO_2$-alkyl, —NH—CO—NH(alkyl), —N(alkyl)-CO—NH(alkyl), —NH—$SO_2$—NH(alkyl), —N(alkyl)-502—NH(alkyl), heterocycloalkyl, or heteroaryl.

8. The compound of claim 7, wherein,
each $R^1$ is independently unsubstituted alkyl, hydroxyalkyl, haloalkyl, aminoalkyl, aryloxyalkyl, heteroaralkyloxyalkyl, unsubstituted alkenyl, alkoxy, acyl, halo, hydroxy, carboxy, cyano, guanadino, amidino, amino, carboxy, mercapto, alkylsulfanyl, alkylsulfinyl, alkylsulfonyl, aminocarbonyl, alkylcarbonylamino, alkoxycarbonyl, alkylcarbonyloxy, alkylsulfonyl, sulfamoyl, cycloalkyl, heterocycloalkyl, (heterocycloalkyl)alkyl, heteroaryl, or heteroaralkyl.

9. The compound of claim 8, wherein,
wherein n is 1 and each $R^2$ is independently guanadino, amidino, —$NH_2$, monoalkylamino, dialkylamino, monocycloalkylamino, monoheterocycloalkylamino, monoheteroarylamino, mono((heterocycloalkyl)alkyl)amino, mono(heteroaralkyl)amino, —NH—CO—NH(alkyl), —N(alkyl)-CO—NH(alkyl), —NH—$SO_2$—NH(alkyl), —N(alkyl)-$SO_2$—NH(alkyl), heterocycloalkyl, or heteroaryl.

10. The compound of claim 7, wherein
wherein $R^2$ is substituted at the 3-position.

11. A compound of claim 9, selected from,
4-(2-pyridin-2-yl-pyrazolo[1,5-a]pyridin-3-yl)-pyrimidin-2-ylamine,
4-[2-(6-methyl-pyridin-2-yl)-pyrazolo[1,5-a]pyridin-3-yl]-pyrimidin-2-ylamine,
2-(6-methyl-pyridin-2-yl)-3-(2-methylsulfanyl-pyrimidin-4-yl)-pyrazolo[1,5-a]pyridine,
4-[2-(6-chloro-pyridin-2-yl)-pyrazolo[1,5-c]pyrimidin-3-yl]-pyrimidin-2-ylamine,
2-(6-methyl-pyridin-2-yl)-3-(2-morpholin-4-yl-pyrimidin-4-yl)-pyrazolo[1,5-c]pyrimidine,
4-[2-(6-methyl-pyridin-2-yl)-pyrazolo[1,5-a]pyrazin-3-yl]-pyrimidin-2-ylamine,
4-[2-(6-methyl-pyridin-2-yl)-pyrazolo[1,5-a]pyrimidin-3-yl]-pyrimidin-2-ylamine,
4-[2-(6-methyl-pyridin-2-yl)-pyrazolo[1,5-c]pyrimidin-3-yl]-pyrimidin-2-ylamine, or a pharmaceutically acceptable salt.

* * * * *